United States Patent
Nesvadba et al.

(10) Patent No.: US 7,160,966 B2
(45) Date of Patent: Jan. 9, 2007

(54) 2,2,6,6 DIETHYL-DIMETHYL-1-ALKOXY-PIPERIDINE COMPOUNDS AND THEIR CORRESPONDING 1-OXIDES

(75) Inventors: Peter Nesvadba, Marly (CH); Marie-Odile Zink, Steinbach (FR); Andreas Kramer, Düdingen (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/048,677

(22) Filed: Feb. 1, 2005

(65) Prior Publication Data

US 2005/0143539 A1    Jun. 30, 2005

Related U.S. Application Data

(62) Division of application No. 10/348,088, filed on Jan. 21, 2003, now Pat. No. 6,891,008, which is a division of application No. 09/811,959, filed on Mar. 19, 2001, now Pat. No. 6,624,306.

(30) Foreign Application Priority Data

Mar. 22, 2000 (EP) ................................. 00810246

(51) Int. Cl.
C08F 2/38 (2006.01)
C08F 2/50 (2006.01)
C08F 4/00 (2006.01)

(52) U.S. Cl. .................. 526/204; 522/9; 252/183.11
(58) Field of Classification Search ............... 546/220; 252/183.11; 526/204; 522/9
See application file for complete search history.

(56) References Cited

U.S. PATENT DOCUMENTS

| 4,141,883 A | 2/1979 | Soma et al. ............... 260/45.8 |
| 4,191,683 A | 3/1980 | Brunetti et al. ............ 260/45.8 |
| 4,581,429 A | 4/1986 | Solomon et al. ............ 526/220 |
| 6,262,206 B1 | 7/2001 | Nesvadba et al. .......... 526/220 |
| 6,353,107 B1 | 3/2002 | Kramer et al. .............. 546/216 |
| 6,683,142 B1 * | 1/2004 | Kramer et al. .............. 526/204 |

FOREIGN PATENT DOCUMENTS

| GB | 2335190 | 9/1999 |
| WO | 98/13392 | 4/1998 |
| WO | 98/30601 | 7/1998 |
| WO | 98/44008 | 10/1998 |
| WO | 00/14134 | 3/2000 |

OTHER PUBLICATIONS

Patent Abstracts of Japan Publication No. 2000072718 (2000).

* cited by examiner

*Primary Examiner*—Bernard Dentz
(74) *Attorney, Agent, or Firm*—Tyler A. Stevenson

(57) ABSTRACT

The present invention relates to selected 1-alkoxy-2,2 diethyl-6,6 dimethyl piperidine and 1-alkoxy-2,6 diethyl-2,3,6 trimethyl piperidine derivatives which are substituted in the 4 position by an oxygen or nitrogen atom; a polymerizable composition comprising a) at least one ethylenically unsaturated monomer and b) said piperidine derivatives. Further aspects of the present invention are a process for polymerizing ethylenically unsaturated monomers, and the use of 1-alkoxy-2,2 diethyl-6,6 dimethyl piperidine and 1-alkoxy-2,6 diethyl-2,6 dimethyl piperidine derivatives which are substituted in the 4 position by an oxygen or nitrogen atom for controlled polymerization. The intermediate N-oxyl derivatives, a composition of the N-oxyl derivatives with ethylenically unsaturated monomers and a free radical initiator, as well as a process for polymerization are also subjects of the present invention.

2 Claims, No Drawings

2,2,6,6 DIETHYL-DIMETHYL-1-ALKOXY-PIPERIDINE COMPOUNDS AND THEIR CORRESPONDING 1-OXIDES

This is a divisional of U.S. application Ser. No. 10/348,088, filed Jan. 21, 2003, now U.S. Pat. No. 6,891,008, which is a divisional of U.S. application Ser. No. 09/811,959, filed Mar. 19, 2001, now U.S. Pat. No. 6,624,306.

The present invention relates to selected 1-alkoxy-2,2 diethyl-6,6 dimethyl piperidine and 1-alkoxy-2,6 diethyl-2,3,6 trimethyl piperidine derivatives which are substituted in the 4 position by an oxygen or nitrogen atom; a polymerizable composition comprising a) at least one ethylenically unsaturated monomer and b) said piperidine derivatives. Further aspects of the present invention are a process for polymerizing ethylenically unsaturated monomers, and the use of 1-alkoxy-2,2 diethyl-6,6 dimethyl piperidine and 1-alkoxy-2,6 diethyl-2,3,6 trimethyl piperidine derivatives which are substituted in the 4 position by an oxygen or nitrogen atom for controlled polymerization. The intermediate N-oxyl derivatives, a composition of the N-oxyl derivatives with ethylenically unsaturated monomers and a free radical initiator, as well as a process for polymerization are also subjects of the present invention.

The compounds of the present invention provide polymeric resin products having low polydispersity. The polymerization process proceeds with good monomer to polymer conversion efficiency. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O. groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine. However, the suggested compounds do not fulfill all requirements. Particularly the polymerization of acrylates does not proceed fast enough and/or the monomer to polymer conversion is not as high as desired.

Recently other attempts to develop new polymerization regulators have been published. WO 98/4408 and WO 98/30601 disclose heterocyclic compounds suitable for controlled polymerization processes. WO 98/13392 discloses open chain alkoxyamines which are derived from NO gas or from nitroso compounds.

GB 2335190 discloses polymerization regulators/initiators on the basis of 2,2,6,6-tetraalkylpiperidine, wherein the alkyl groups have from 1 to 6 carbon atoms and at least one group is different from methyl.

It has now been found, that amongst those 2,2,6,6-tetraalkylpiperidines generically disclosed in GB 2335190 those are of particular value which are derivatives of 1-alkoxy-2,2 diethyl-6,6 dimethyl piperidine and of 1-alkoxy-2,6 diethyl-2,3,6 trimethyl piperidine and which are substituted in the 4 position by an oxygen or nitrogen atom, which itself is further substituted.

The steric hindrance introduced by the two diethyl groups leads to an optimized balance in terms of stability of the compounds, initiating activity and control of polymerization.

The particular substitution pattern in 2 and 6 position of the piperidine ring allows high monomer to polymer conversions in short times and low polydispersities which are generally below 2. High monomer to polymer conversions are even achieved with acrylates, such as ethyl- or butyl-acrylate. The temperature necessary to achieve high conversion in short times may be for example as low as 120° C.

The compounds exhibit an unchanged initiating/regulating activity even after storage at elevated temperatures as for example used in conventional stability tests.

The oxygen or nitrogen atom in the 4 position of the piperidine ring allows a variety of substitutions. This may for example be used to adjust secondary properties such as the compound's polarity and hence its compatibility with the monomer, oligomer and polymer mixture or also its volatility.

One subject of the present invention is a compound according to formula Ia or IIa

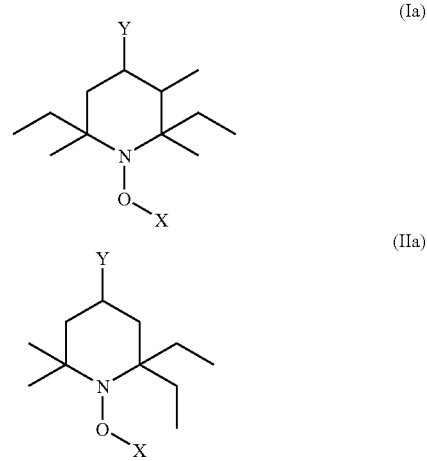

wherein
  Y is a radical

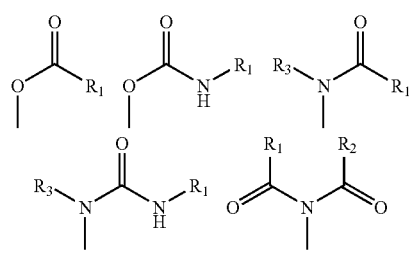

$R_1$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH, —COO($C_1$–$C_4$)alkyl, $C_2$–$C_{18}$alkyl which may be interrupted by one or more oxygen atom, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl)

$R_2$ is hydrogen, $C_1$–$C_{18}$alkyl or $R_1$ and $R_2$ together with the nitrogen atom form a 5-membered ring which may have an unsaturated bond or be fused to a benzene ring;

$R_3$ is hydrogen or $C_1$–$C_{18}$alkyl; and

X is selected from the group consisting of —($C_5$–$C_{12}$)-3-cycloalkenyl, —$CH_2$-phenyl, $CH_3CH$-phenyl, $(CH_3)_2C$-phenyl, $(C_5$–$C_6$cycloalkyl$)_2$CCN, $(CH_3)_2$CCN, —$CH_2CH$=$CH_2$, $CH_3CH$—$CH$=$CH_2$, ($C_1$–$C_4$alkyl)$CR_{20}$—C(O)-phenyl, ($C_1$–$C_4$)alkyl-$CR_{20}$—C(O)—($C_1$–$C_4$) alkoxy, ($C_1$–$C_4$)alkyl-$CR_{20}$—C(O)—($C_1$–$C_4$)alkyl, ($C_1$–$C_4$) alkyl-$CR_{20}$—C(O)—N-di($C_1$–$C_4$)alkyl, ($C_1$–$C_4$)alkyl-$CR_{20}$—C(O)—NH($C_1$–$C_4$)alkyl, ($C_1$–$C_4$)alkyl-$CR_{20}$—C(O)—$NH_2$, wherein $R_{20}$ is hydrogen or ($C_1$–$C_4$)alkyl; with the proviso that benzoic acid 2,6-diethyl-2,3,6-trimethyl-1-(1-phenyl-ethoxy)-piperidin-4-yl ester is excluded.

$C_1$–$C_{18}$alkyl can be linear or branched. Examples are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$–$C_{18}$alkyl interrupted by —O— are for example 3-oxapentane, 4-oxaheptane, 3,6-dioxaoctane, 4,7-dioxadecane, 4,9-dioxadodecane, 3,6,9-trioxaundecane and 4,7,10-trioxatridecane.

Alkyl substituted by a group —COOH is for example $CH_2$—COOH, $CH_2$—$CH_2$—COOH, $(CH_2)_3$—COOH or $CH_2$—CHCOOH—$CH_2$—$CH_3$ Examples of alkoxy containing not more than 8 carbon atoms are methoxy, ethoxy, propoxy, isopropoxy, butoxy, isobutoxy, pentoxy, isopentoxy, hexoxy, heptoxy or octoxy.

$C_2$–$C_4$alkenyl is for example ethenyl, propenyl or butenyl; preferably ethenyl or —C($CH_3$)=$CH_2$.

Cyclohexyl substituted by COOH is for example cyclohexane-carbonic acid.

Phenyl substituted by COOH is for example benzoic acid.

Phenyl substituted by $C_1$–$C_4$alkyl is for example toluene or xylene.

Preferably X is —$CH_2$-phenyl, $CH_3CH$-phenyl,

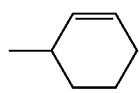

(3-cyclohexenyl) or $(CH_3)_2C$-phenyl.

More preferably X is $CH_3CH$-phenyl.

Preferred compounds are of formulae Ia or IIa wherein Y is a radical of formula

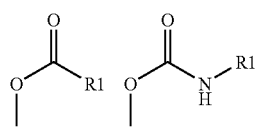

and $R_1$ has the meaning as defined above.

Particularly preferred are the following individual compounds.

Compounds according to formula (Ia).

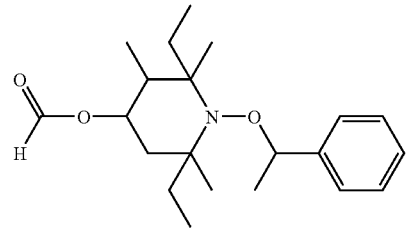

(1)

Formic acid 2,6-diethyl-2,3,6-trimethyl-1-(1-phenyl-ethoxy)-piperidin-4-yl ester;

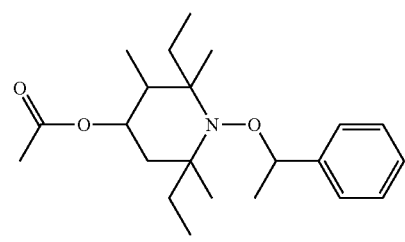

(2)

Acetic acid 2,6-diethyl-2,3,6-trimethyl-1-(1-phenyl-ethoxy)-piperidin-4-yl ester;

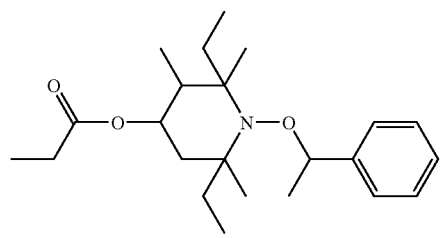

(3)

Propionic acid 2,6-diethyl-2,3,6-trimethyl-1-(1-phenyl-ethoxy)-piperidin-4-yl ester;

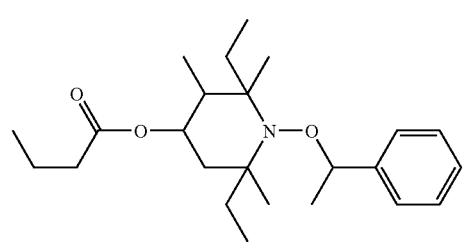

(4)

Butyric acid 2,6-diethyl-2,3,6-trimethyl-1-(1-phenyl-ethoxy)-piperidin-4-yl ester;

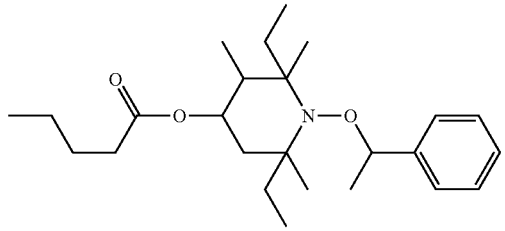
(5)

Pentanoic acid 2,6-diethyl-2,3,6-trimethyl-1-(1-phenyl-ethoxy)-piperidin-4-yl ester;

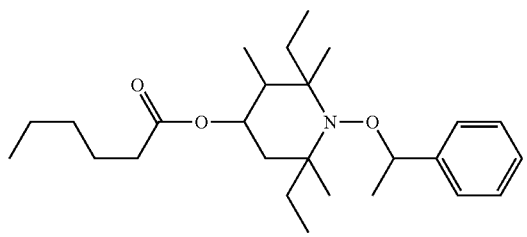
(6)

Hexanoic acid 2,6-diethyl-2,3,6-trimethyl-1-(1-phenyl-ethoxy)-piperidin-4-yl ester;

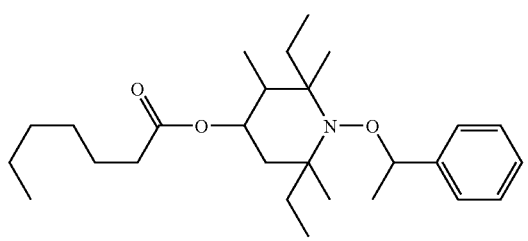
(7)

Heptanoic acid 2,6-diethyl-2,3,6-trimethyl-1-(1-phenyl-ethoxy)-piperidin-4-yl ester;

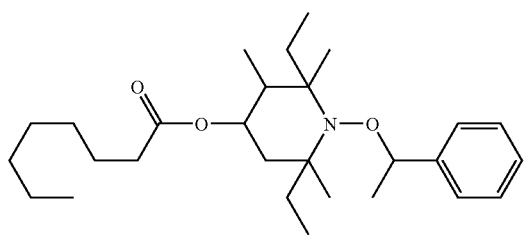
(8)

Octanoic acid 2,6-diethyl-2,3,6-trimethyl-1-(1-phenyl-ethoxy)-piperidin-4-yl ester;

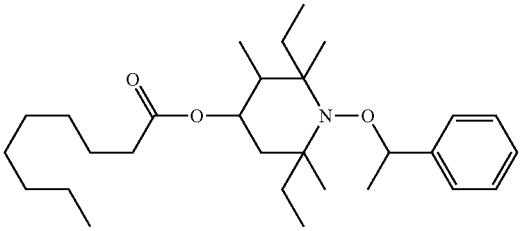
(9)

Nonanoic acid 2,6-diethyl-2,3,6-trimethyl-1-(1-phenyl-ethoxy)-piperidin-4-yl ester;

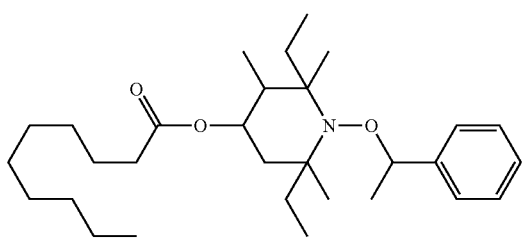
(10)

Decanoic acid 2,6-diethyl-2,3,6-trimethyl-1-(1-phenyl-ethoxy)-piperidin-4-yl ester;

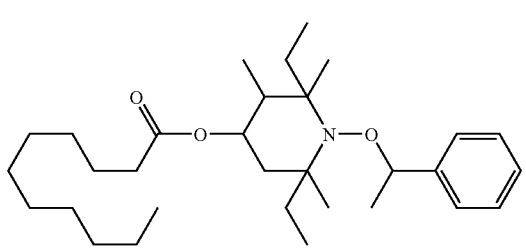
(11)

Undecanoic acid 2,6-diethyl-2,3,6-trimethyl-1-(1-phenyl-ethoxy)-piperidin-4-yl ester;

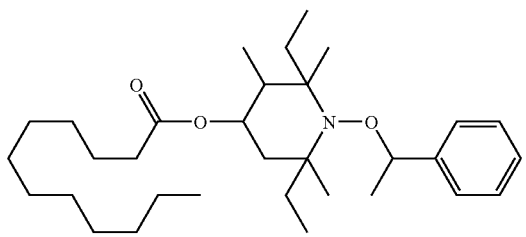
(12)

Dodecanoic acid 2,6-diethyl-2,3,6-trimethyl-1-(1-phenyl-ethoxy)-piperidin-4-yl ester;

Pentadecanoic acid 2,6-diethyl-2,3,6-trimethyl-1-(1-phenyl-ethoxy)-piperidin-4-yl ester;

(13)

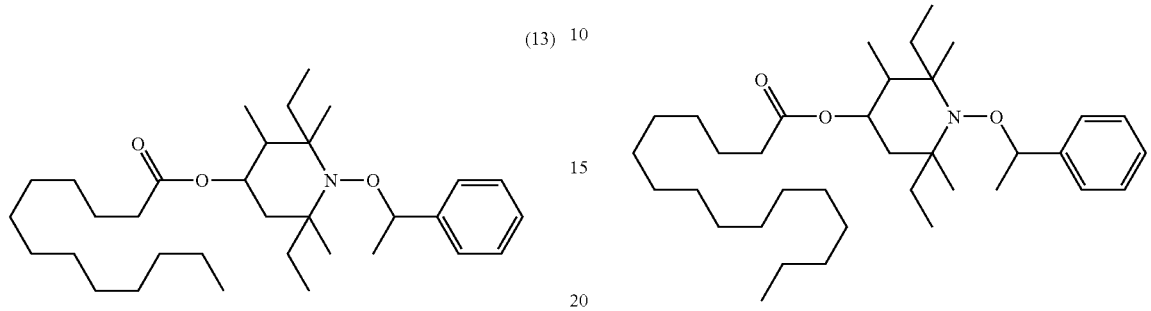

Tridecanoic acid 2,6-diethyl-2,3,6-trimethyl-1-(1-phenyl-ethoxy)-piperidin-4-yl ester;

(16)

Hexadecanoic acid 2,6-diethyl-2,3,6-trimethyl-1-(1-phenyl-ethoxy)-piperidin-4-yl ester;

(14)

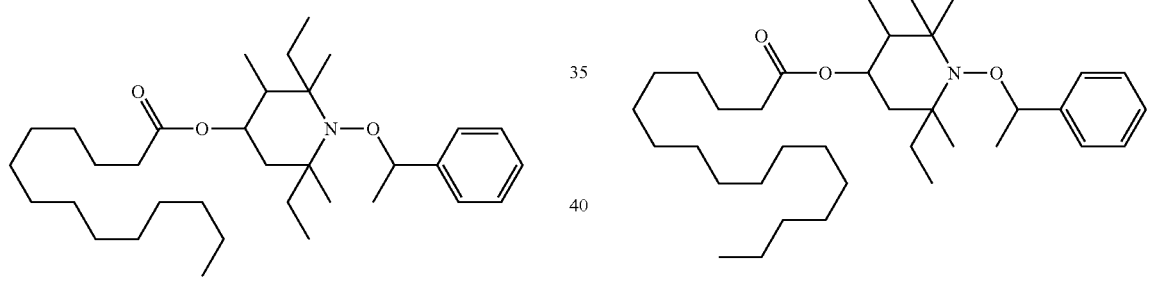

Tetradecanoic acid 2,6-diethyl-2,3,6-trimethyl-1-(1-phenyl-ethoxy)-piperidin-4-yl ester;

(17)

Heptadecanoic acid 2,6-diethyl-2,3,6-trimethyl-1-(1-phenyl-ethoxy)-piperidin-4-yl ester;

(15)

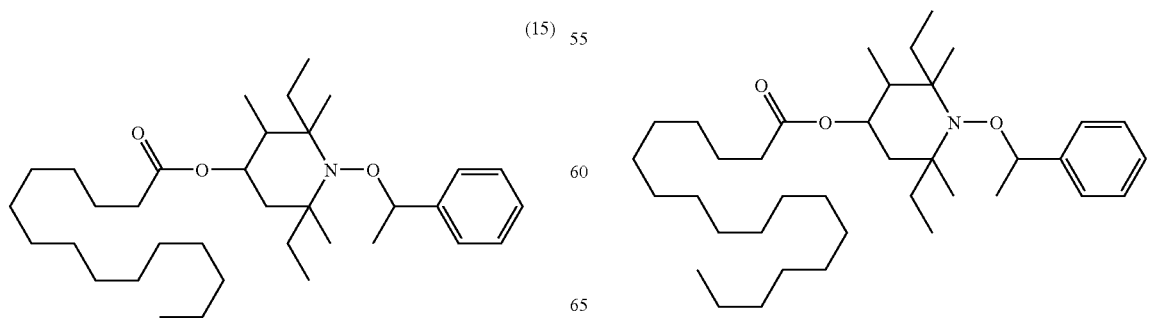

(18)

Octadecanoic acid 2,6-diethyl-2,3,6-trimethyl-1-(1-phenyl-ethoxy)-piperidin-4-yl ester;

Carbonic acid .tert.-butyl ester 2,6-diethyl-2,3,6-trimethyl-1-(1-phenyl-ethoxy)-piperidin-4-yl ester;

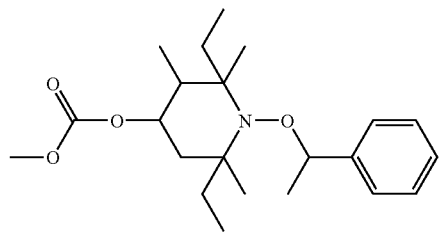
(19)

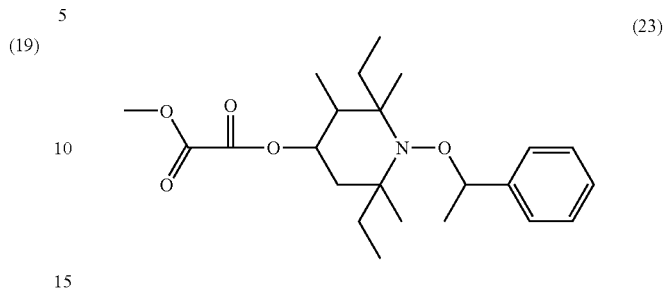
(23)

Carbonic acid 2,6-diethyl-2,3,6-trimethyl-1-(1-phenyl-ethoxy)-piperidin-4-yl ester methyl ester;

Oxalic acid 2,6-diethyl-2,3,6-trimethyl-1-(1-phenyl-ethoxy)-piperidin-4-yl ester methyl ester;

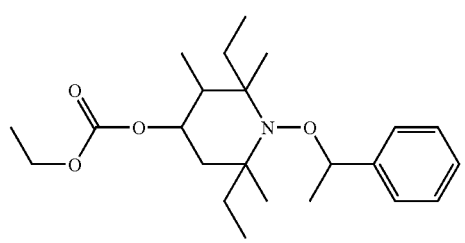
(20)

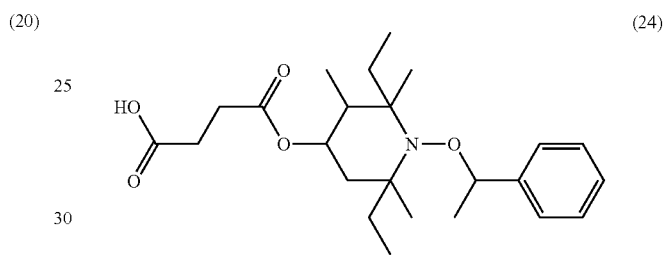
(24)

Carbonic acid 2,6-diethyl-2,3,6-trimethyl-1-(1-phenyl-ethoxy)-piperidin-4-yl ester ethyl ester;

Succinic acid mono-[2,6-diethyl-2,3,6-trimethyl-1-(1-phenyl-ethoxy)-piperidin-4-yl]ester;

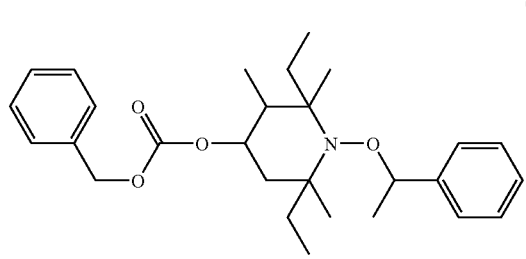
(21)

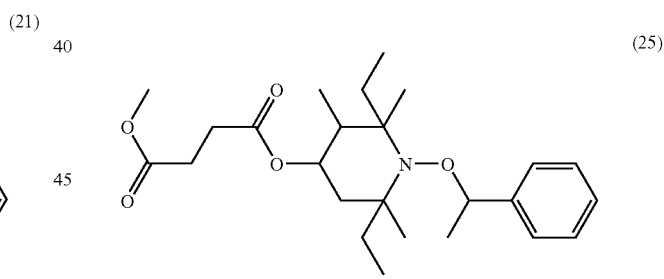
(25)

Carbonic acid benzyl ester 2,6-diethyl-2,3,6-trimethyl-1-(1-phenyl-ethoxy)-piperidin-4-yl ester;

Succinic acid 2,6-diethyl-2,3,6-trimethyl-1-(1-phenyl-ethoxy)-piperidin-4-yl ester methyl ester;

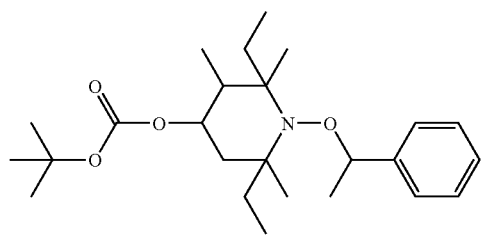
(22)

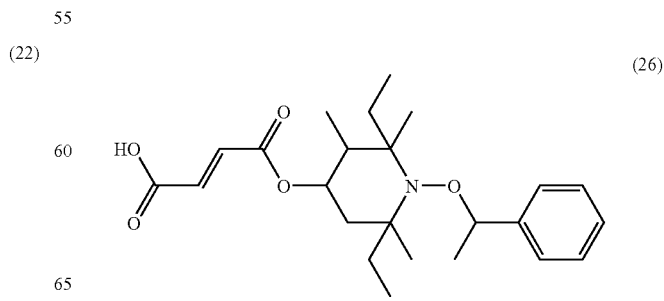
(26)

But-2-enedioic acid mono-[2,6-diethyl-2,3,6-trimethyl-1-(1-phenyl-ethoxy)-piperidin-4-yl]ester;

(27)

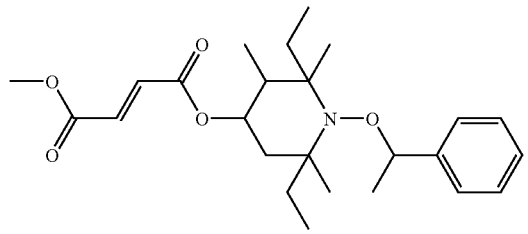

But-2-enedioic acid 2,6-diethyl-2,3,6-trimethyl-1-(1-phenyl-ethoxy)-piperidin-4-yl ester methyl ester;

(28)

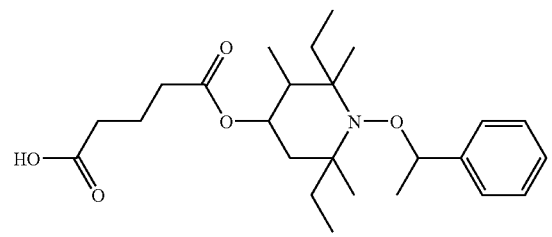

Pentanedioic acid mono-[2,6-diethyl-2,3,6-trimethyl-1-(1-phenyl-ethoxy)-piperidin-4-yl]ester;

(29)

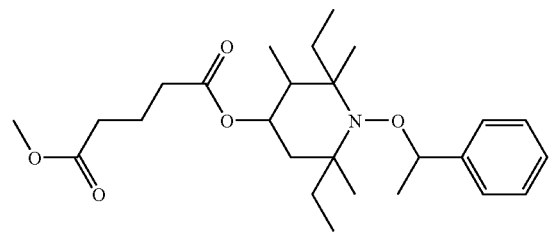

Pentanedioic acid 2,6-diethyl-2,3,6-trimethyl-1-(1-phenyl-ethoxy)-piperidin-4-yl ester methyl ester (30)

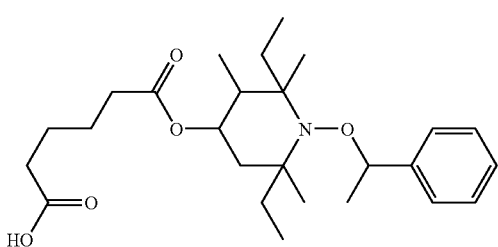

Hexanedioic acid mono-[2,6-diethyl-2,3,6-trimethyl-1-(1-phenyl-ethoxy)-piperidin-4-yl]ester;

(31)

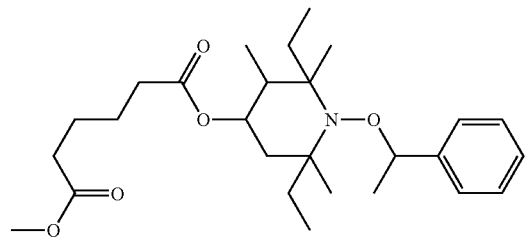

Hexanedioic acid 2,6-diethyl-2,3,6-trimethyl-1-(1-phenyl-ethoxy)-piperidin-4-yl ester methyl ester;

(32)

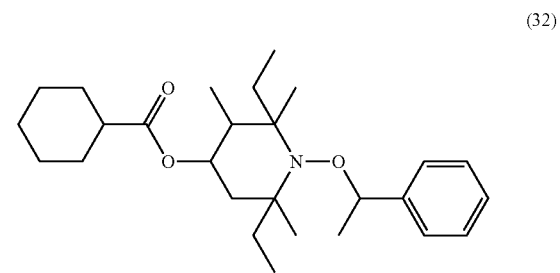

Cyclohexanecarboxylic acid 2,6-diethyl-2,3,6-trimethyl-1-(1-phenyl-ethoxy)-piperidin-4-yl ester;

(33)

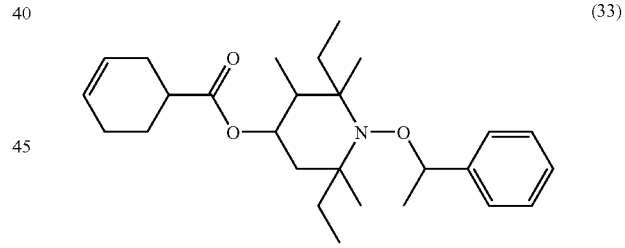

Cyclohex-3-enecarboxylic acid 2,6-diethyl-2,3,6-trimethyl-1-(1-phenyl-ethoxy)-piperidin-4-yl ester;

(34)

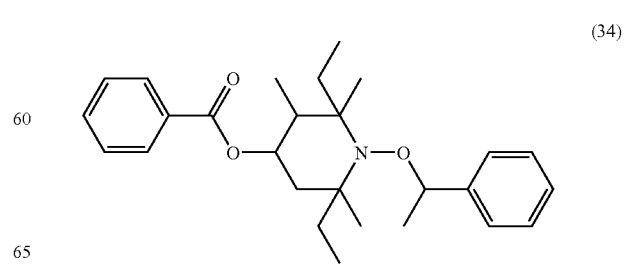

Benzoic acid 2,6-diethyl-2,3,6-trimethyl-1-(1-phenyl-ethoxy)-piperidin-4-yl ester;

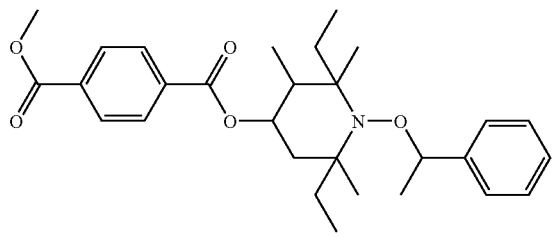
(35)

Terephthalic acid 1-[2,6-diethyl-2,3,6-trimethyl-1-(1-phenyl-ethoxy)-piperidin-4-yl]ester 4-methyl ester;

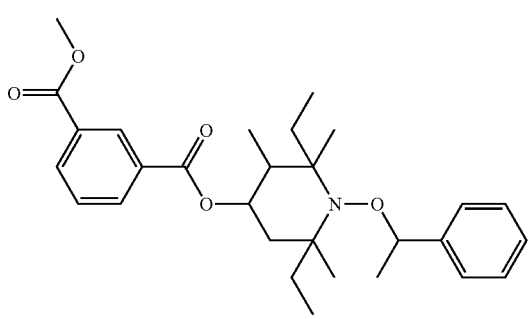
(36)

Isophthalic acid 1-[2,6-diethyl-2,3,6-trimethyl-1-(1-phenyl-ethoxy)-piperidin-4-yl]ester 3-methyl ester;

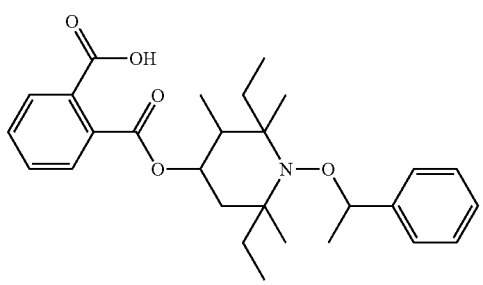
(37)

Phthalic acid mono-[2,6-diethyl-2,3,6-trimethyl-1-(1-phenyl-ethoxy)-piperidin-4-yl]ester;

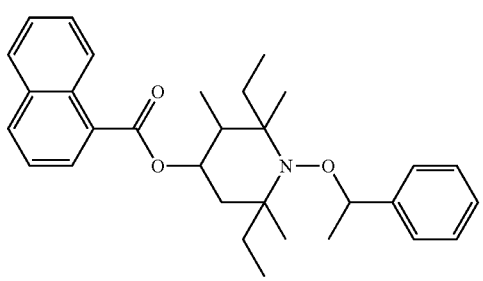
(38)

Naphthalene-1-carboxylic acid 2,6-diethyl-2,3,6-trimethyl-1-(1-phenyl-ethoxy)-piperidin-4-yl ester;

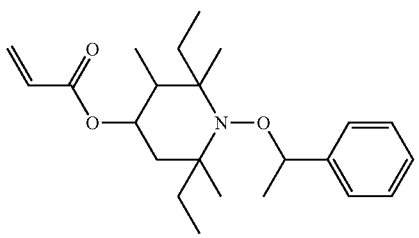
(39)

Acrylic acid 2,6-diethyl-2,3,6-trimethyl-1-(1-phenyl-ethoxy)-piperidin-4-yl ester;

(40)

2-Methyl-acrylic acid 2,6-diethyl-2,3,6-trimethyl-1-(1-phenyl-ethoxy)-piperidin-4-yl ester;

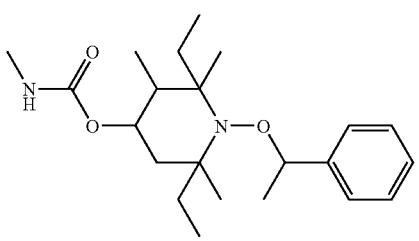
(42)

Methyl-carbamic acid 2,6-diethyl-2,3,6-trimethyl-1-(1-phenyl-ethoxy)-piperidin-4-yl ester;

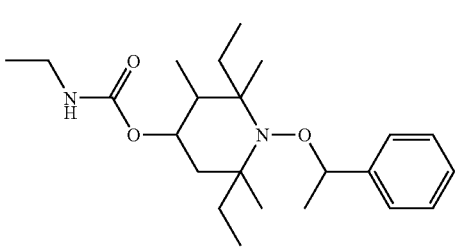
(43)

Ethyl-carbamic acid 2,6-diethyl-2,3,6-trimethyl-1-(1-phenyl-ethoxy)-piperidin-4-yl ester;

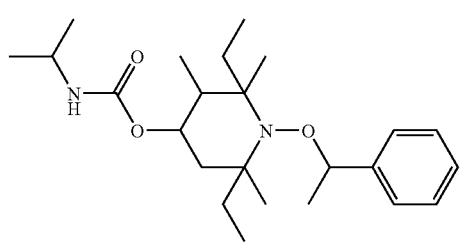
(44)

Isopropyl-carbamic acid 2,6-diethyl-2,3,6-trimethyl-1-(1-phenyl-ethoxy)-piperidin-4-yl ester;

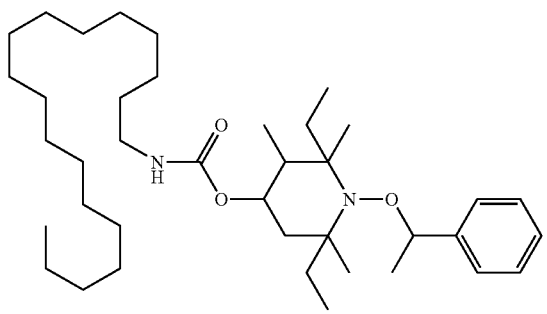
(45)

Octadecyl-carbamic acid 2,6-diethyl-2,3,6-trimethyl-1-(1-phenyl-ethoxy)-piperidin-4-yl ester;

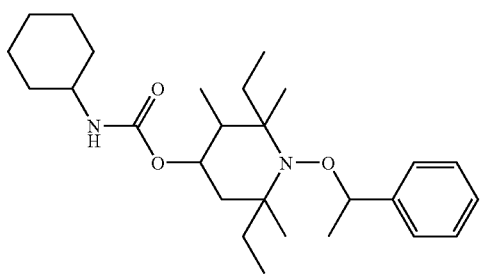
(46)

Cyclohexyl-carbamic acid 2,6-diethyl-2,3,6-trimethyl-1-(1-phenyl-ethoxy)-piperidin-4-yl ester;

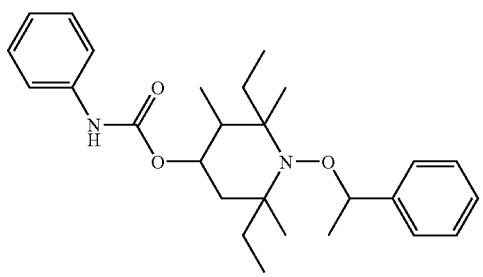
(47)

Phenyl-carbamic acid 2,6-diethyl-2,3,6-trimethyl-1-(1-phenyl-ethoxy)-piperidin-4-yl ester;

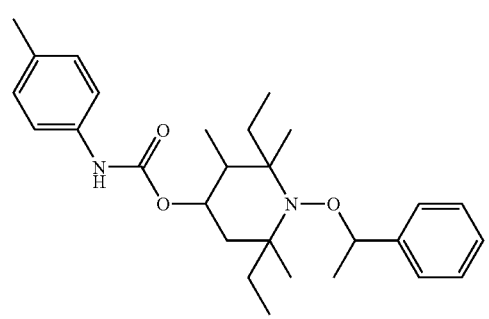
(48)

p-Tolyl-carbamic acid 2,6-diethyl-2,3,6-trimethyl-1-(1-phenyl-ethoxy)-piperidin-4-yl ester;

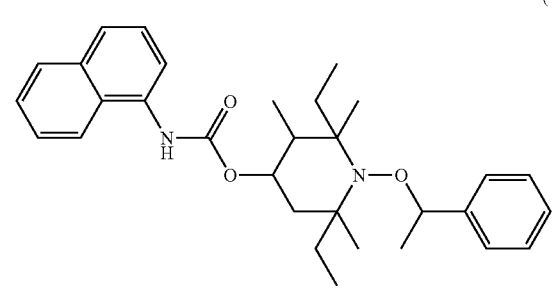
(49)

Naphthalen-1-yl-carbamic acid 2,6-diethyl-2,3,6-trimethyl-1-(1-phenyl-ethoxy)-piperidin-4-yl ester;

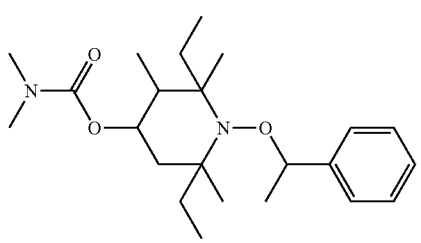
(50)

Dimethyl-carbamic acid 2,6-diethyl-2,3,6-trimethyl-1-(1-phenyl-ethoxy)-piperidin-4-yl ester;

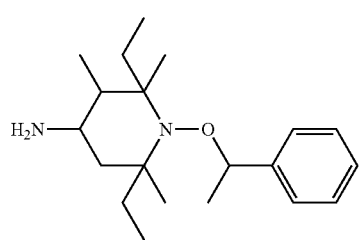
(51)

2,6-Diethyl-2,3,6-trimethyl-1-(1-phenyl-ethoxy)-piperidin-4-ylamine;

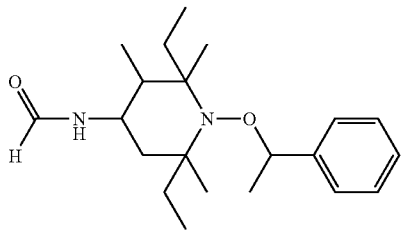
(52)

N-[2,6-Diethyl-2,3,6-trimethyl-1-(1-phenyl-ethoxy)-piperidin-4-yl]-formamide;

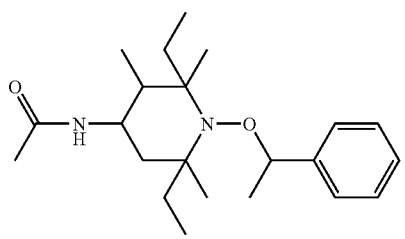
(53)

N-[2,6-Diethyl-2,3,6-trimethyl-1-(1-phenyl-ethoxy)-piperidin-4-yl]-acetamide;

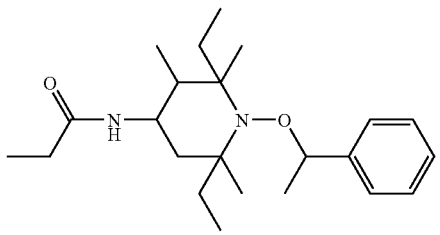
(54)

N-[2,6-Diethyl-2,3,6-trimethyl-1-(1-phenyl-ethoxy)-piperidin-4-yl]-propionamide;

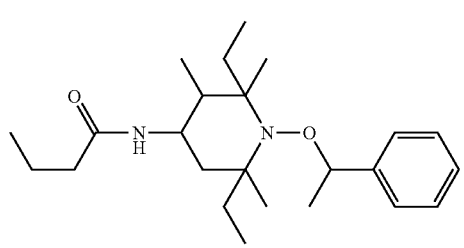
(55)

N-[2,6-Diethyl-2,3,6-trimethyl-1-(1-phenyl-ethoxy)-piperidin-4-yl]-butyramide;

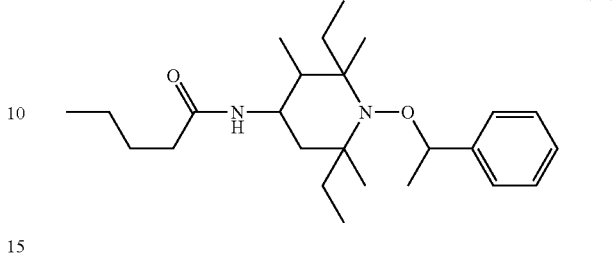
(56)

Pentanoic acid [2,6-diethyl-2,3,6-trimethyl-1-(1-phenyl-ethoxy)-piperidin-4-yl]-amide;

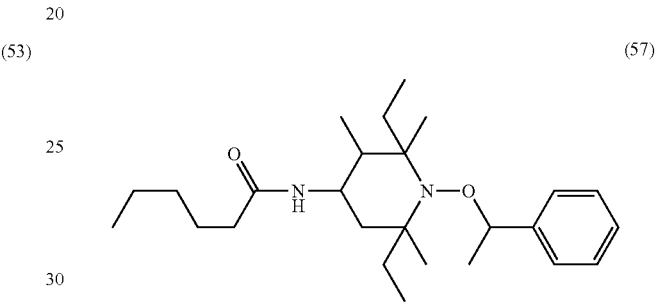
(57)

Hexanoic acid [2,6-diethyl-2,3,6-trimethyl-1-(1-phenyl-ethoxy)-piperidin-4-yl]-amide;

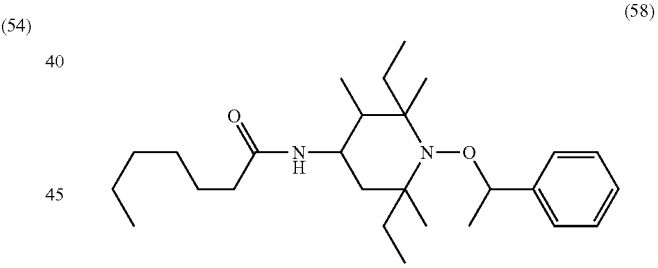
(58)

Heptanoic acid [2,6-diethyl-2,3,6-trimethyl-1-(1-phenyl-ethoxy)-piperidin-4-yl]-amide;

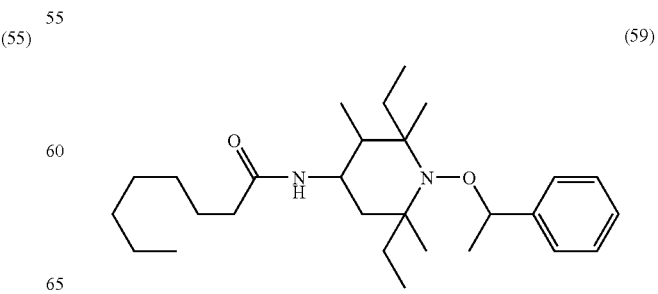
(59)

Octanoic acid [2,6-diethyl-2,3,6-trimethyl-1-(1-phenyl-ethoxy)-piperidin-4-yl]-amide;

(60)
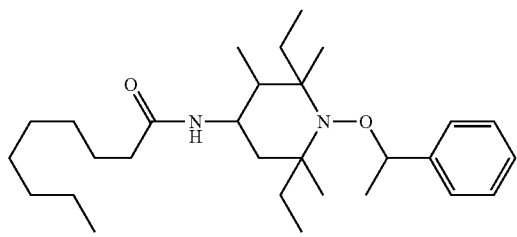

Nonanoic acid [2,6-diethyl-2,3,6-trimethyl-1-(1-phenyl-ethoxy)-piperidin-4-yl]-amide;

(61)
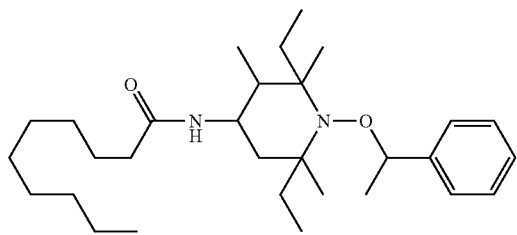

Decanoic acid [2,6-diethyl-2,3,6-trimethyl-1-(1-phenyl-ethoxy)-piperidin-4-yl]-amide;

(62)
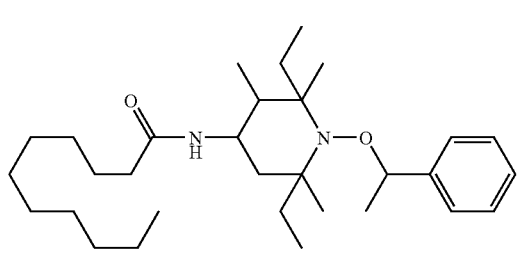

Undecanoic acid [2,6-diethyl-2,3,6-trimethyl-1-(1-phenyl-ethoxy)-piperidin-4-yl]-amide;

(63)
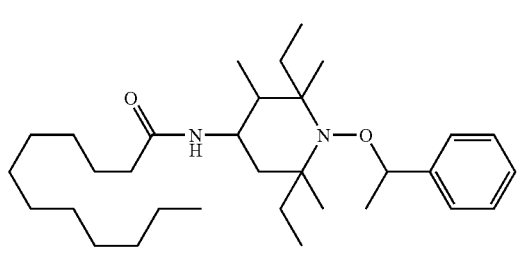

Dodecanoic acid [2,6-diethyl-2,3,6-trimethyl-1-(1-phenyl-ethoxy)-piperidin-4-yl]-amide;

(64)
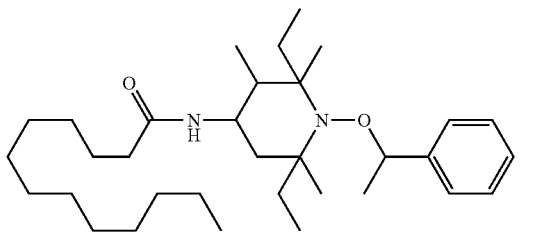

Tridecanoic acid [2,6-diethyl-2,3,6-trimethyl-1-(1-phenyl-ethoxy)-piperidin-4-yl]-amide;

(65)
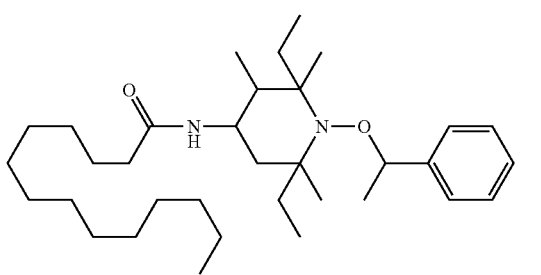

Tetradecanoic acid [2,6-diethyl-2,3,6-trimethyl-1-(1-phenyl-ethoxy)-piperidin-4-yl]-amide;

(66)
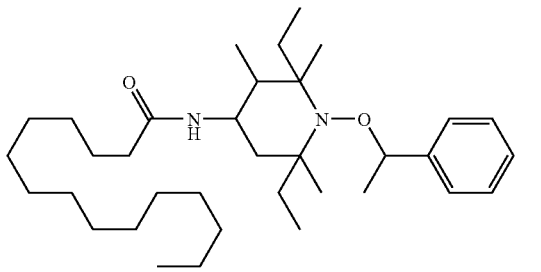

Pentadecanoic acid [2,6-diethyl-2,3,6-trimethyl-1-(1-phenyl-ethoxy)-piperidin-4-yl]-amide;

(67)
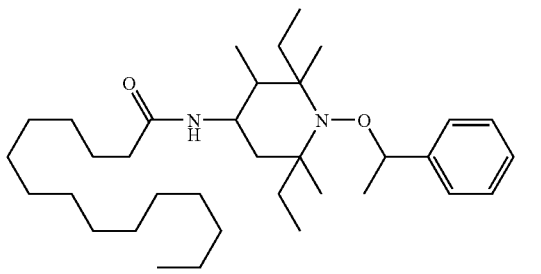

Hexadecanoic acid [2,6-diethyl-2,3,6-trimethyl-1-(1-phenyl-ethoxy)-piperidin-4-yl]-amide;

(68)

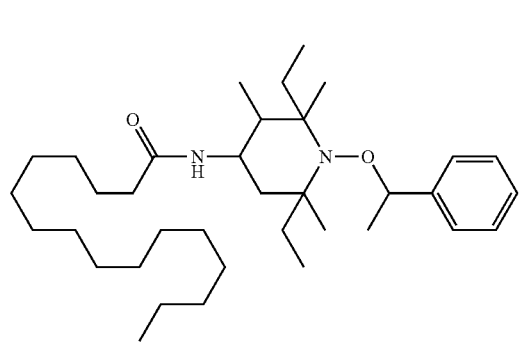

Heptadecanoic acid [2,6-diethyl-2,3,6-trimethyl-1-(1-phenyl-ethoxy)-piperidin-4-yl]-amide;

(69)

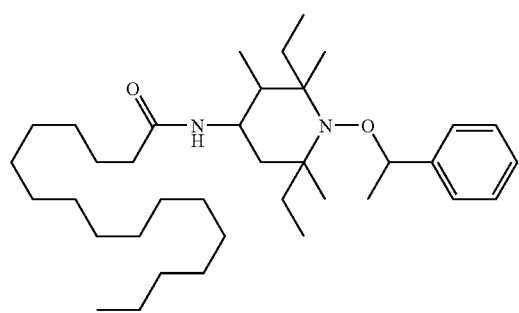

Octadecanoic acid [2,6-diethyl-2,3,6-trimethyl-1-(1-phenyl-ethoxy)-piperidin-4-yl]-amide;

(70)

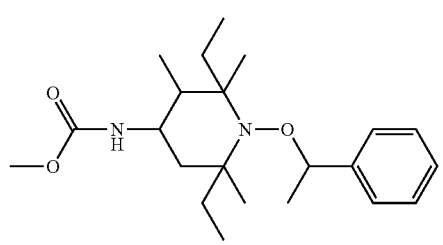

[2,6-Diethyl-2,3,6-trimethyl-1-(1-phenyl-ethoxy)-piperidin-4-yl]-carbamic acid methyl ester;

(71)

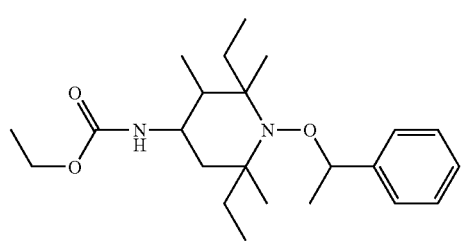

[2,6-Diethyl-2,3,6-trimethyl-1-(1-phenyl-ethoxy)-piperidin-4-yl]-carbamic acid ethyl ester;

(72)

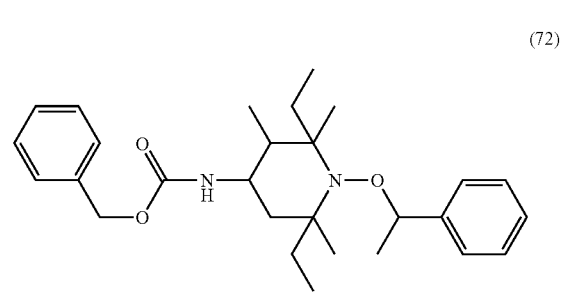

[2,6-Diethyl-2,3,6-trimethyl-1-(1-phenyl-ethoxy)-piperidin-4-yl]-carbamic acid benzyl ester;

(73)

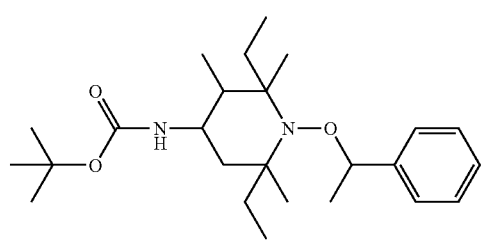

[2,6-Diethyl-2,3,6-trimethyl-1-(1-phenyl-ethoxy)-piperidin-4-yl]-carbamic acid .tert.-butyl ester;

(74)

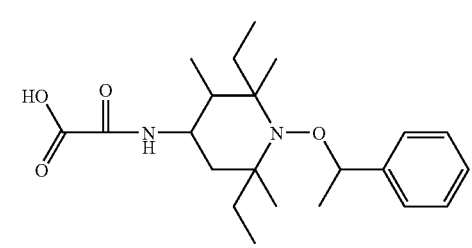

N-[2,6-Diethyl-2,3,6-trimethyl-1-(1-phenyl-ethoxy)-piperidin-4-yl]-oxalamic acid;

(75)

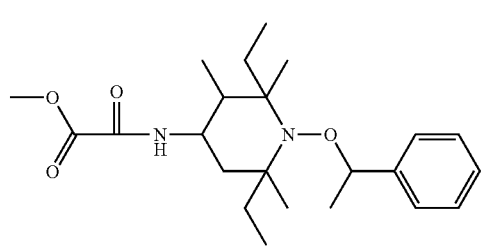

N-[2,6-Diethyl-2,3,6-trimethyl-1-(1-phenyl-ethoxy)-piperidin-4-yl]-oxalamic acid methyl ester;

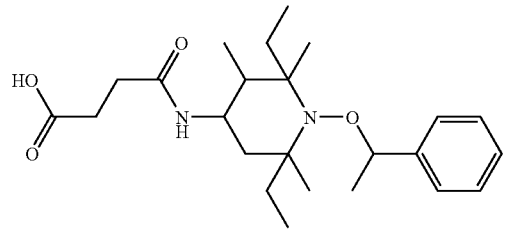

(76)

N-[2,6-Diethyl-2,3,6-trimethyl-1-(1-phenyl-ethoxy)-piperidin-4-yl]-succinamic acid;

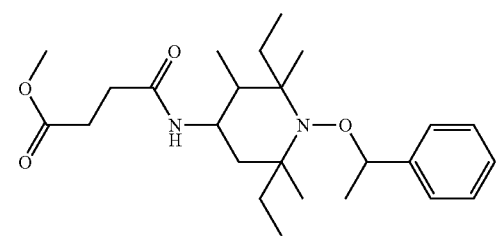

(77)

N-[2,6-Diethyl-2,3,6-trimethyl-1-(1-phenyl-ethoxy)-piperidin-4-yl]-succinamic acid methyl ester;

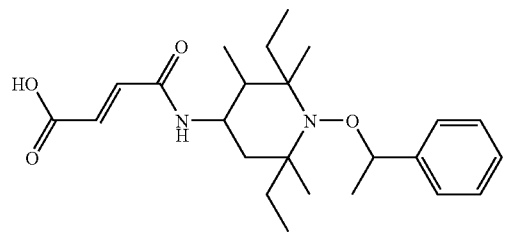

(78)

3-[2,6-Diethyl-2,3,6-trimethyl-1-(1-phenyl-ethoxy)-piperidin-4-ylcarbamoyl]-acrylic acid;

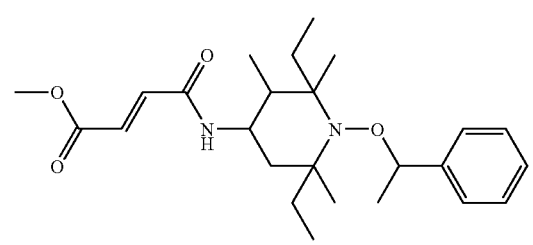

(79)

3-[2,6-Diethyl-2,3,6-trimethyl-1-(1-phenyl-ethoxy)-piperidin-4-ylcarbamoyl]-acrylic acid methyl ester;

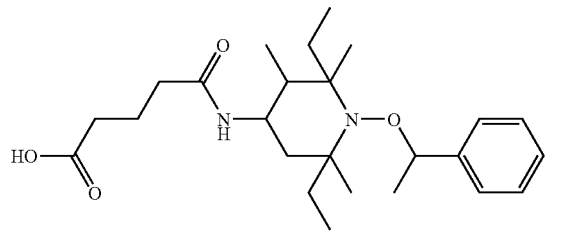

(80)

4-[2,6-Diethyl-2,3,6-trimethyl-1-(1-phenyl-ethoxy)-piperidin-4-ylcarbamoyl]-butyric acid;

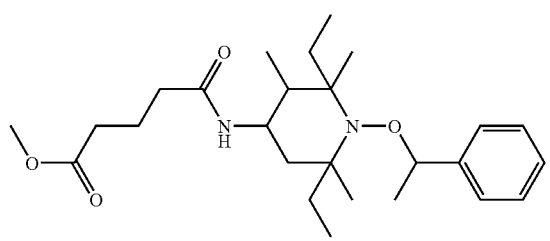

(81)

4-[2,6-Diethyl-2,3,6-trimethyl-1-(1-phenyl-ethoxy)-piperidin-4-ylcarbamoyl]-butyric acid methyl ester;

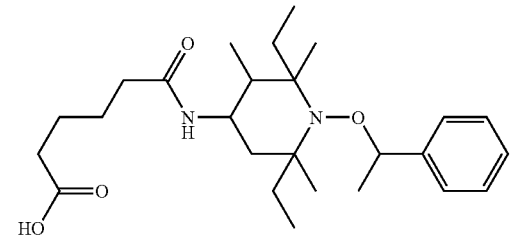

(82)

5-[2,6-Diethyl-2,3,6-trimethyl-1-(1-phenyl-ethoxy)-piperidin-4-ylcarbamoyl]-pentanoic acid;

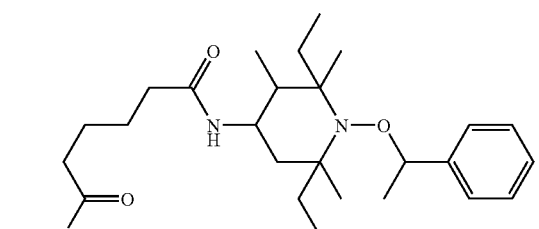

(83)

5-[2,6-Diethyl-2,3,6-trimethyl-1-(1-phenyl-ethoxy)-piperidin-4-ylcarbamoyl]-pentanoic acid methyl ester;

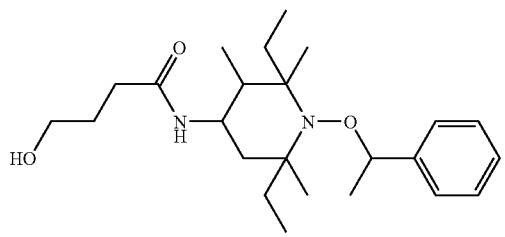
(84)

N-[2,6-Diethyl-2,3,6-trimethyl-1-(1-phenyl-ethoxy)-piperidin-4-yl]-4-hydroxy-butyramide;

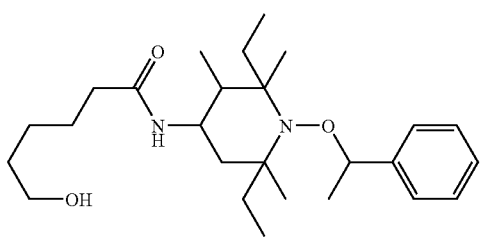
(85)

6-Hydroxy-hexanoic acid [2,6-diethyl-2,3,6-trimethyl-1-(1-phenyl-ethoxy)-piperidin-4-yl]-amide;

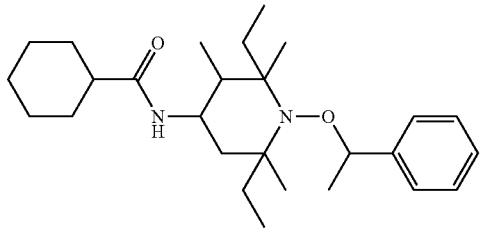
(86)

Cyclohexanecarboxylic acid [2,6-diethyl-2,3,6-trimethyl-1-(1-phenyl-ethoxy)-piperidin-4-yl]-amide;

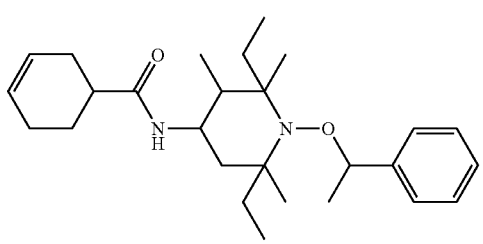
(87)

Cyclohex-3-enecarboxylic acid [2,6-diethyl-2,3,6-trimethyl-1-(1-phenyl-ethoxy)-piperidin-4-yl]-amide;

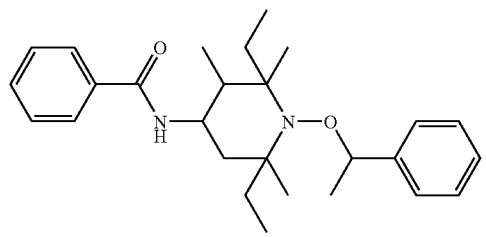
(88)

N-[2,6-Diethyl-2,3,6-trimethyl-1-(1-phenyl-ethoxy)-piperidin-4-yl]-benzamide;

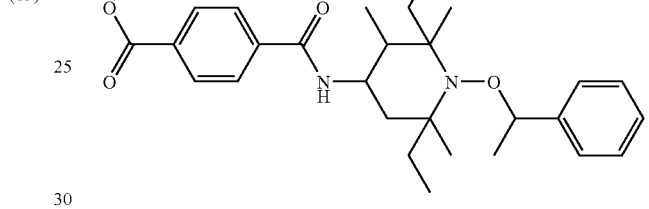
(89)

N-[2,6-Diethyl-2,3,6-trimethyl-1-(1-phenyl-ethoxy)-piperidin-4-yl]-terephthalamic acid methyl ester;

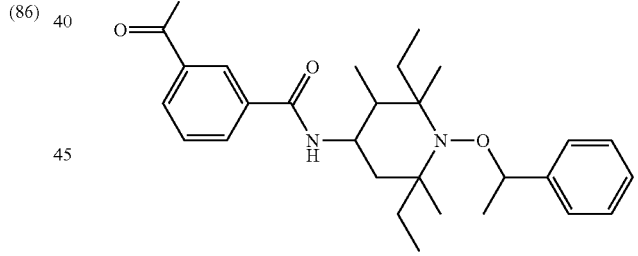
(90)

N-[2,6-Diethyl-2,3,6-trimethyl-1-(1-phenyl-ethoxy)-piperidin-4-yl]-4-isophthalamic acid methyl ester;

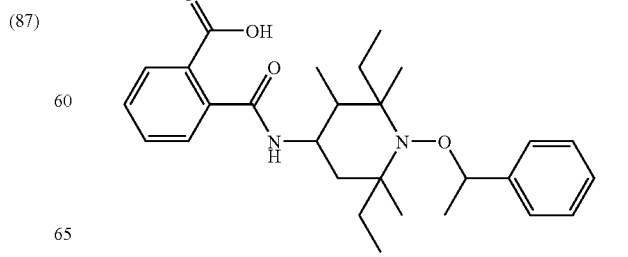
(91)

N-[2,6-Diethyl-2,3,6-trimethyl-1-(1-phenyl-ethoxy)-piperidin-4-yl]-phthalamic acid

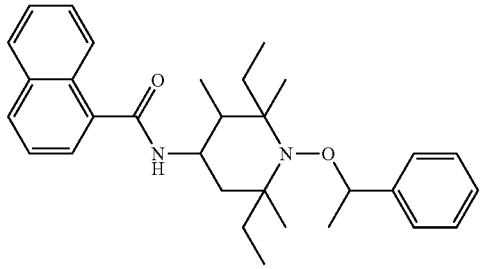
(92)

Naphthalene-1-carboxylic acid [2,6-diethyl-2,3,6-trimethyl-1-(1-phenyl-ethoxy)-piperidin-4-yl]-amide;

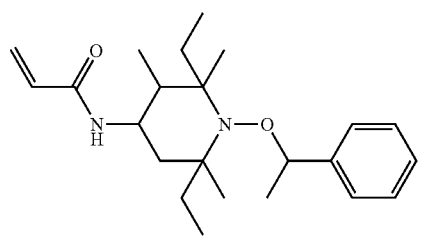
(93)

N-[2,6-Diethyl-2,3,6-trimethyl-1-(1-phenyl-ethoxy)-piperidin-4-yl]-acrylamide;

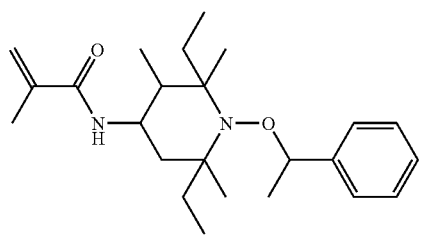
(94)

N-[2,6-Diethyl-2,3,6-trimethyl-1-(1-phenyl-ethoxy)-piperidin-4-yl]-2-methyl-acrylamide;

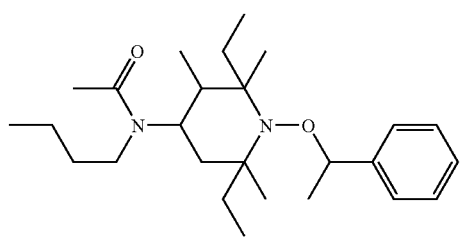
(95)

N-Butyl-N-[2,6-diethyl-2,3,6-trimethyl-1-(1-phenyl-ethoxy)-piperidin-4-yl]-acetamide

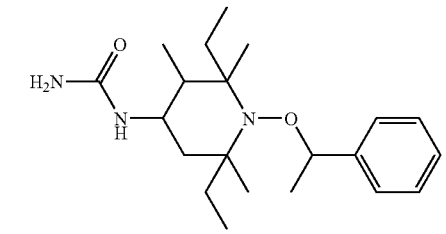
(96)

[2,6-Diethyl-2,3,6-trimethyl-1-(1-phenyl-ethoxy)-piperidin-4-yl]-urea;

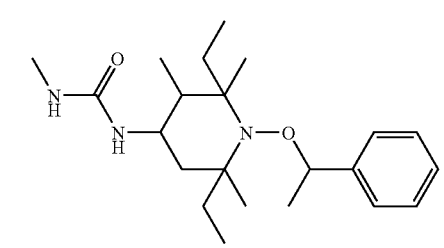
(97)

1-[2,6-Diethyl-2,3,6-trimethyl-1-(1-phenyl-ethoxy)-piperidin-4-yl]methyl-urea;

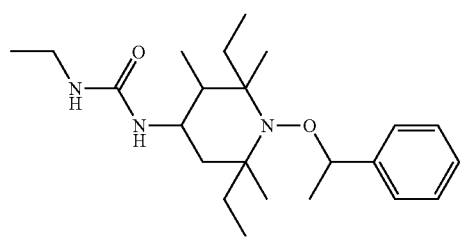
(98)

1-[2,6-Diethyl-2,3,6-trimethyl-1-(1-phenyl-ethoxy)-piperidin-4-yl]-3-ethyl-urea;

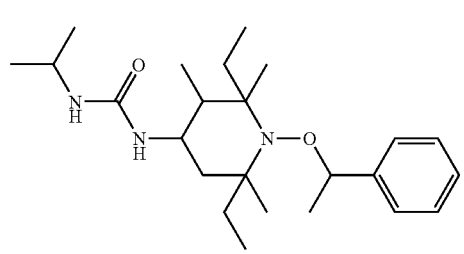
(99)

1-[2,6-Diethyl-2,3,6-trimethyl-1-(1-phenyl-ethoxy)-piperidin-4-yl]-3-isopropyl-urea;

1-[2,6-Diethyl-2,3,6-trimethyl-1-(1-phenyl-ethoxy)-piperidin-4-yl]-3-.p.-tolyl-urea;

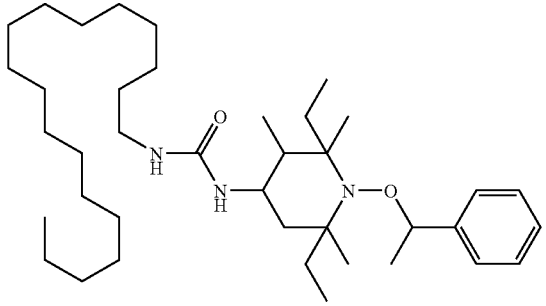
(100)

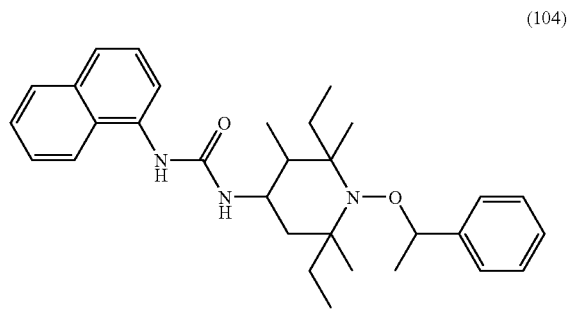
(104)

1-[2,6-Diethyl-2,3,6-trimethyl-1-(1-phenyl-ethoxy)-piperidin-4-yl]-3-octadecyl-urea;

1-[2,6-Diethyl-2,3,6-trimethyl-1-(1-phenyl-ethoxy)-piperidin-4-yl]-3-naphthalen-1-yl-urea;

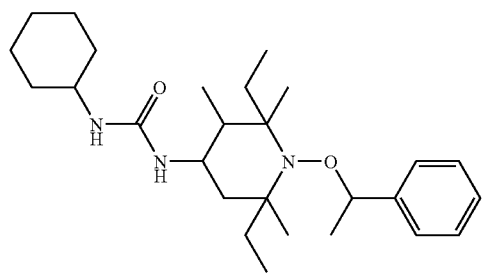
(101)

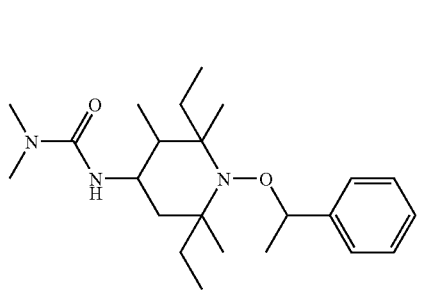
(105)

1-Cyclohexyl-3-[2,6-diethyl-2,3,6-trimethyl-1-(1-phenyl-ethoxy)-piperidin-4-yl]-urea;

3-[2,6-Diethyl-2,3,6-trimethyl-1-(1-phenyl-ethoxy)-piperidin-4-yl]-1,1-dimethyl-urea;

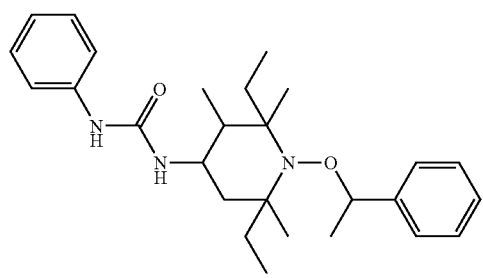
(102)

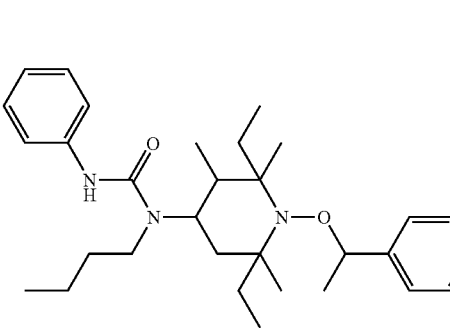
(106)

1-[2,6-Diethyl-2,3,6-trimethyl-1-(1-phenyl-ethoxy)-piperidin-4-yl]-3-phenyl-urea;

1-Butyl-1-[2,6-diethyl-2,3,6-trimethyl-1-(1-phenyl-ethoxy)-piperidin-4-yl]-3-phenyl-urea;

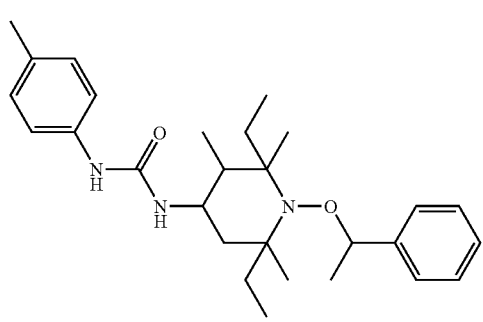
(103)

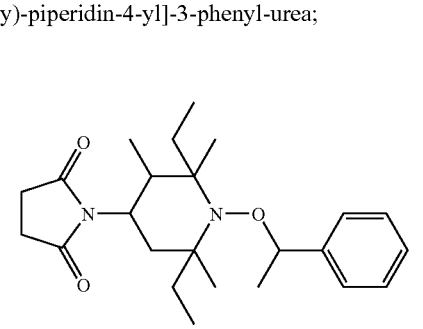
(107)

1-[2,6-Diethyl-2,3,6-trimethyl-1-(1-phenyl-ethoxy)-piperidin-4-yl]-pyrrolidine-2,5-dione;

2-[2,6-Diethyl-2,3,6-trimethyl-1-(1-phenyl-ethoxy)-piperidin-4-yl]-isoindole-1,3-dione;

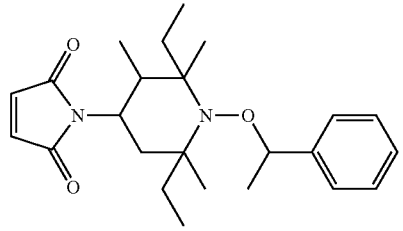
(108)

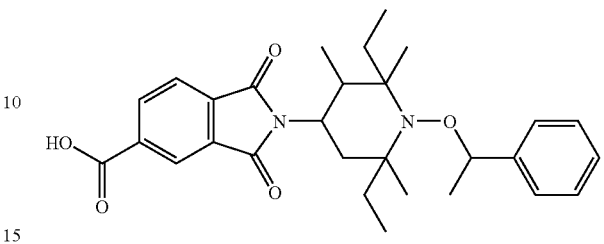
(112)

1-[2,6-Diethyl-2,3,6-trimethyl-1-(1-phenyl-ethoxy)-piperidin-4-yl]-pyrrole-2,5-dione;

2-[2,6-Diethyl-2,3,6-trimethyl-1-(1-phenyl-ethoxy)-piperidin-4-yl]-1,3-dioxo-2,3-dihydro-1.H.-isoindole-5-carboxylic acid.

Also particularly preferred are the following individual compounds according to formula (IIa).

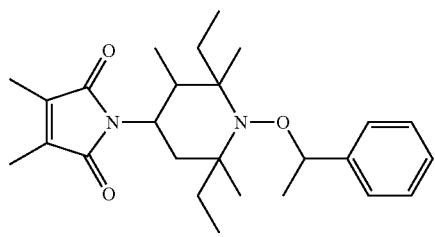
(109)

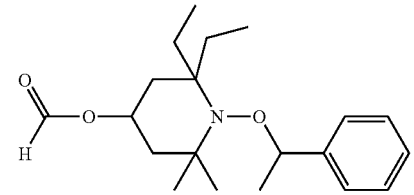
(1)

1-[2,6-Diethyl-2,3,6-trimethyl-1-(1-phenyl-ethoxy)-piperidin-4-yl]-3,4-dimethyl-pyrrole-2,5-dione;

Formic acid 2,2-diethyl-6,6-dimethyl-1-(1-phenyl-ethoxy)-piperidin-4-yl ester;

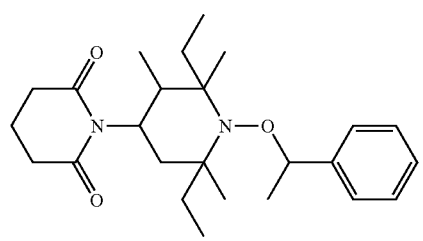
(110)

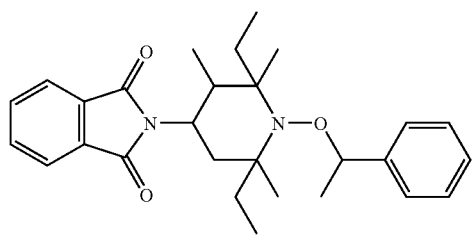
(2)

2',6'-Diethyl-2',3',6'-trimethyl-1'-(1-phenyl-ethoxy)-[1,4']bipiperidinyl-2,6-dione;

Acetic acid 2,2-diethyl-6,6-dimethyl-1-(1-phenyl-ethoxy)-piperidin-4-yl ester;

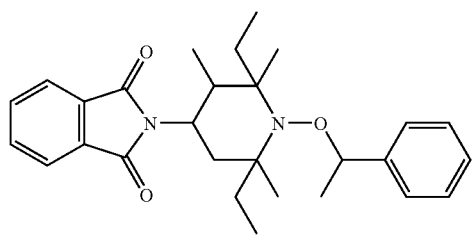
(111)

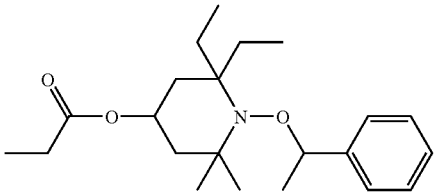
(3)

Propionic acid 2,2-diethyl-6,6-dimethyl-1-(1-phenyl-ethoxy)-piperidin-4-yl ester;

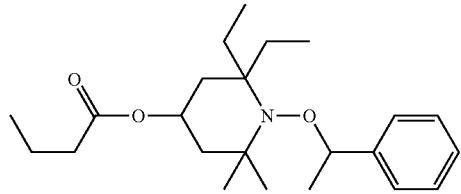
(4)

Butyric acid 2,2-diethyl-6,6-dimethyl-1-(1-phenyl-ethoxy)-piperidin-4-yl ester;

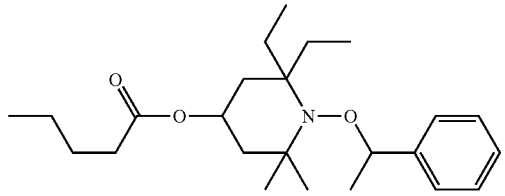
(5)

Pentanoic acid 2,2-diethyl-6,6-dimethyl-1-(1-phenyl-ethoxy)-piperidin-4-yl ester;

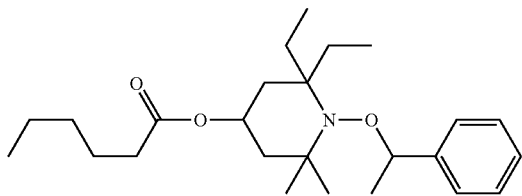
(6)

Hexanoic acid 2,2-diethyl-6,6-dimethyl-1-(1-phenyl-ethoxy)-piperidin-4-yl ester;

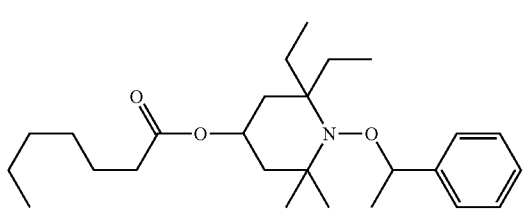
(7)

Heptanoic acid 2,2-diethyl-6,6-dimethyl-1-(1-phenyl-ethoxy)-piperidin-4-yl ester;

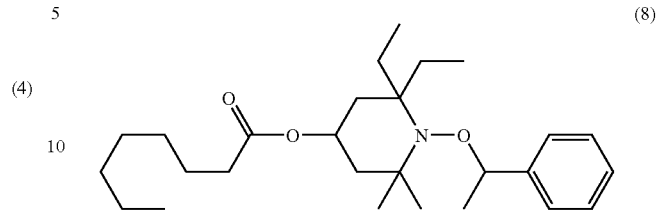
(8)

Octanoic acid 2,2-diethyl-6,6-dimethyl-1-(1-phenyl-ethoxy)-piperidin-4-yl ester;

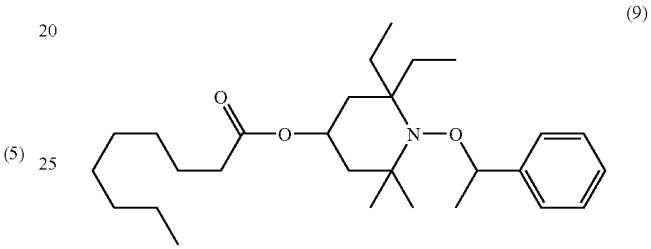
(9)

Nonanoic acid 2,2-diethyl-6,6-dimethyl-1-(1-phenyl-ethoxy)-piperidin-4-yl ester;

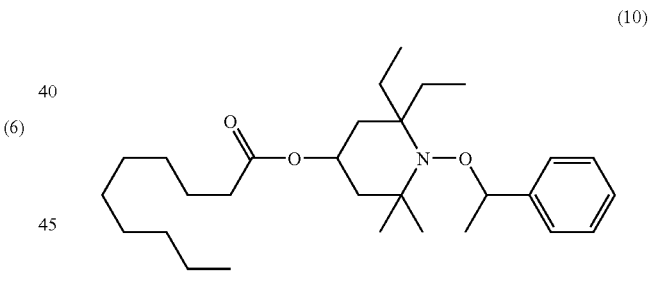
(10)

Decanoic acid 2,2-diethyl-6,6-dimethyl-1-(1-phenyl-ethoxy)-piperidin-4-yl ester;

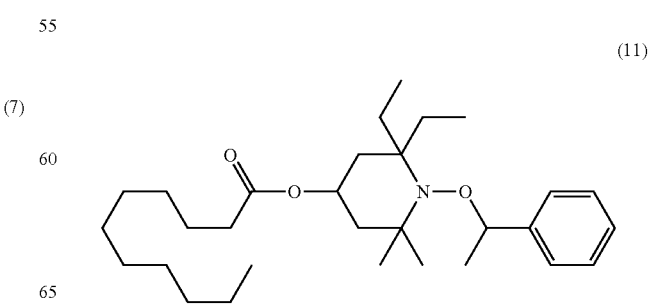
(11)

Undecanoic acid 2,2-diethyl-6,6-dimethyl-1-(1-phenyl-ethoxy)-piperidin-4-yl ester, (12)

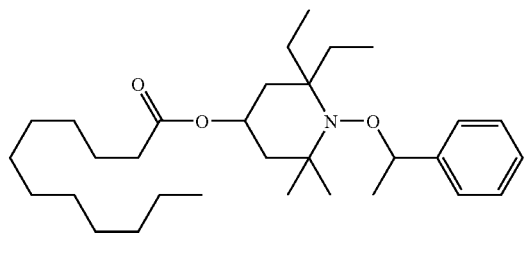

Dodecanoic acid 2,2-diethyl-6,6-dimethyl-1-(1-phenyl-ethoxy)-piperidin-4-yl ester;

(13)

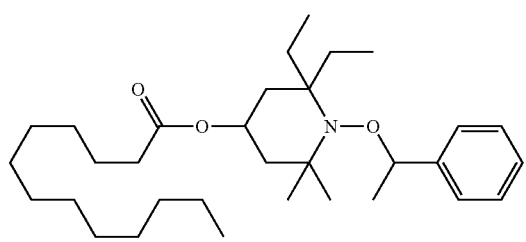

Tridecanoic acid 2,2-diethyl-6,6-dimethyl-1-(1-phenyl-ethoxy)-piperidin-4-yl ester;

(14)

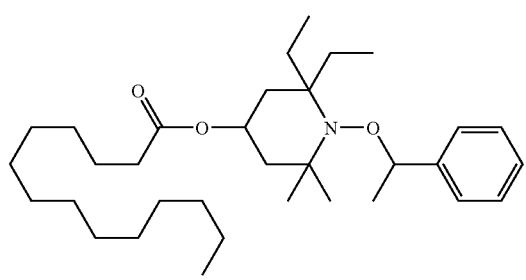

Tetradecanoic acid 2,2-diethyl-6,6-dimethyl-1-(1-phenyl-ethoxy)-piperidin-4-yl ester;

(15)

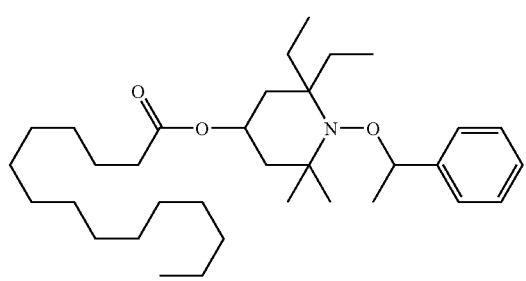

Pentadecanoic acid 2,2-diethyl-6,6-dimethyl-1-(1-phenyl-ethoxy)-piperidin-4-yl ester;

(16)

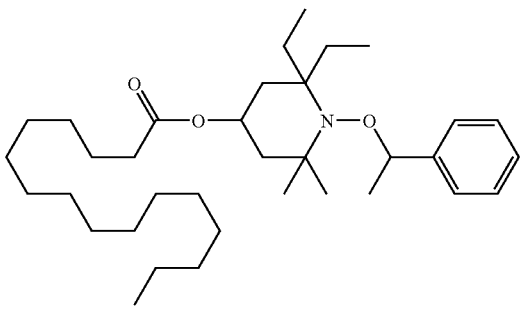

Hexadecanoic acid 2,2-diethyl-6,6-dimethyl-1-(1-phenyl-ethoxy)-piperidin-4-yl ester;

(17)

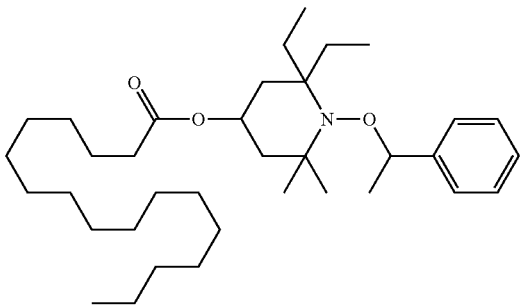

Heptadecanoic acid 2,2-diethyl-6,6-dimethyl-1-(1-phenyl-ethoxy)-piperidin-4-yl ester;

(18)

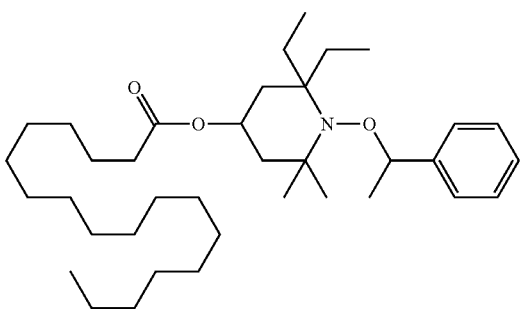

Octadecanoic acid 2,2-diethyl-6,6-dimethyl-1-(1-phenyl-ethoxy)-piperidin-4-yl ester;

Carbonic acid .tert.-butyl ester 2,2-diethyl-6,6-dimethyl-1-(1-phenyl-ethoxy)-piperidin-4-yl ester;

(19)
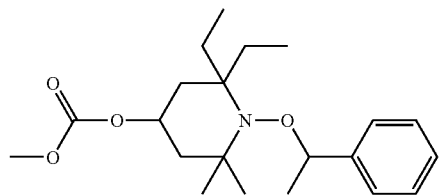

Carbonic acid 2,2-diethyl-6,6-dimethyl-1-(1-phenyl-ethoxy)-piperidin-4-yl ester methyl ester;

(23)
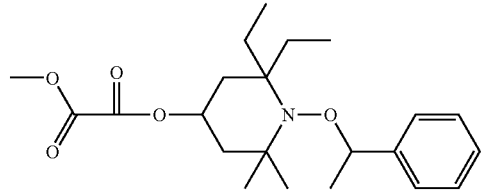

Oxalic acid 2,2-diethyl-6,6-dimethyl-1-(1-phenylethoxy)-piperidin-4-yl ester methyl ester;

(20)
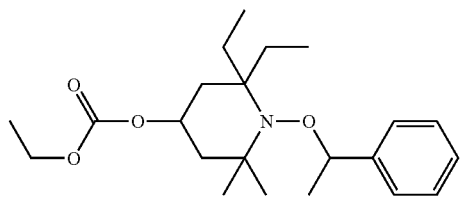

Carbonic acid 2,2-diethyl-6,6-dimethyl-1-(1-phenyl-ethoxy)-piperidin-4-yl ester ethyl ester;

(24)
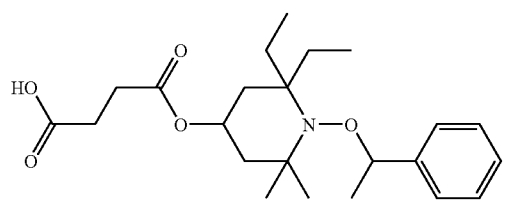

Succinic acid mono-[2,2-diethyl-6,6-dimethyl-1-(1-phenyl-ethoxy)-piperidin-4-yl]ester;

(21)
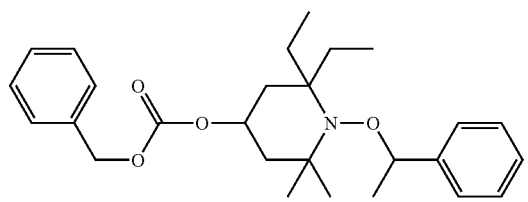

Carbonic acid benzyl ester 2,2-diethyl-6,6-dimethyl-1-(1-phenyl-ethoxy)-piperidin-4-yl ester;

(25)
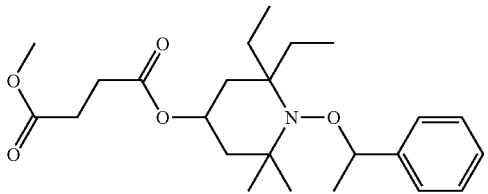

Succinic acid 2,2-diethyl-6,6-dimethyl-1-(1-phenyl-ethoxy)-piperidin-4-yl ester methyl ester;

(22)
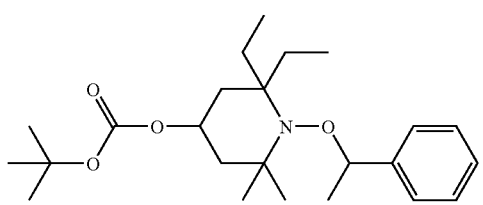

(26)
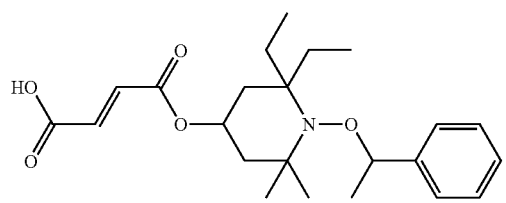

But-2-enedioic acid mono-[2,2-diethyl-6,6-dimethyl-1-(1-phenyl-ethoxy)-piperidin-4-yl]ester;

(27)

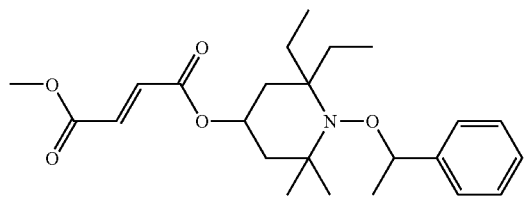

But-2-enedioic acid 2,2-diethyl-6,6-dimethyl-1-(1-phenyl-ethoxy)-piperidin-4-yl ester methyl ester;

(28)

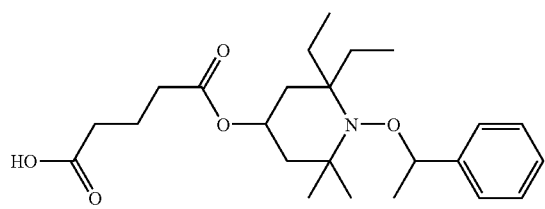

Pentanedioic acid mono-[2,2-diethyl-6,6-dimethyl-1-(1-phenyl-ethoxy)-piperidin-4-yl]ester;

(29)

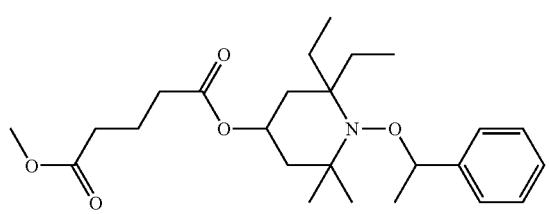

Pentanedioic acid 2,2-diethyl-6,6-dimethyl-1-(1-phenyl-ethoxy)-piperidin-4-yl ester methyl ester;

(30)

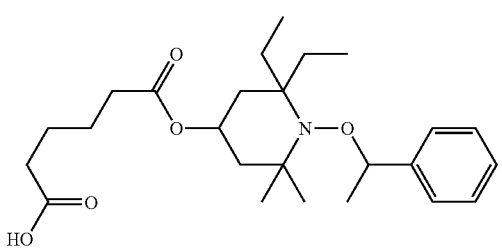

Hexanedioic acid mono-[2,2-diethyl-6,6-dimethyl-1-(1-phenyl-ethoxy)-piperidin-4-yl]ester;

(31)

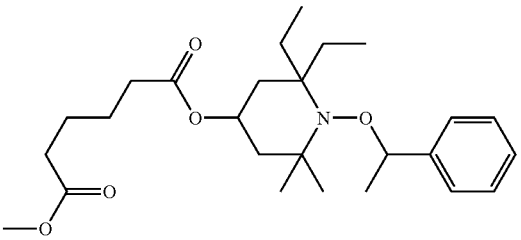

Hexanedioic acid 2,2-diethyl-6,6-dimethyl-1-(1-phenyl-ethoxy)-piperidin-4-yl ester methyl ester;

(32)

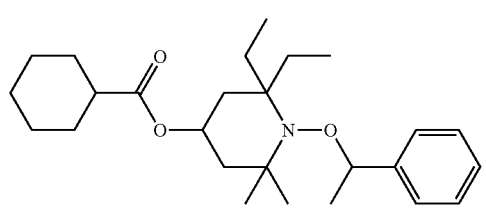

Cyclohexanecarboxylic acid 2,2-diethyl-6,6-dimethyl-1-(1-phenyl-ethoxy)-piperidin-4-yl ester;

(33)

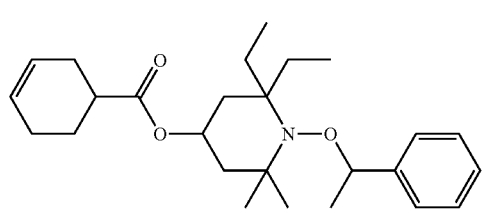

Cyclohex-3-enecarboxylic acid 2,2-diethyl-6,6-dimethyl-1-(1-phenyl-ethoxy)-piperidin-4-yl ester;

(34)

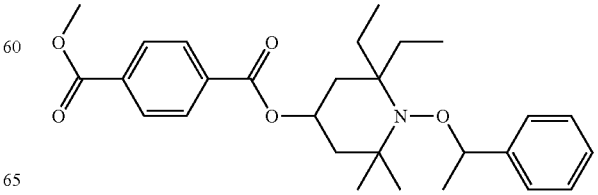

Terephthalic acid 1-[2,2-diethyl-6,6-dimethyl-1-(1-phenyl-ethoxy)-piperidin-4-yl]ester 4-methyl ester;

Acrylic acid 2,2-diethyl-6,6-dimethyl-1-(1-phenyl-ethoxy)-piperidin-4-yl ester;

(35)

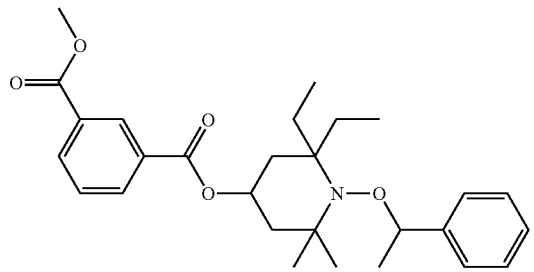

Isophthalic acid 1-[2,2-diethyl-6,6-dimethyl-1-(1-phenyl-ethoxy)-piperidin-4-yl]ester 3-methyl ester;

(39)

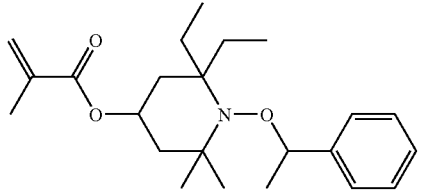

2-Methyl-acrylic acid 2,2-diethyl-6,6-dimethyl-1-(1-phenyl-ethoxy)-piperidin-4-yl ester;

(36)

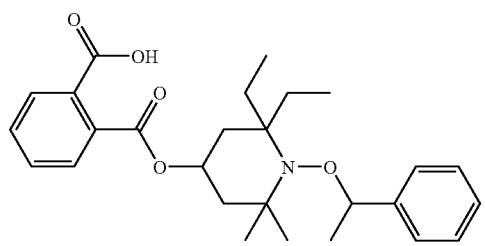

Phthalic acid mono-[2,2-diethyl-6,6-dimethyl-1-(1-phenyl-ethoxy)-piperidin-4-yl]ester;

(41)

Methyl-carbamic acid 2,2-diethyl-6,6-dimethyl-1-(1-phenyl-ethoxy)-piperidin-4-yl ester;

(37)

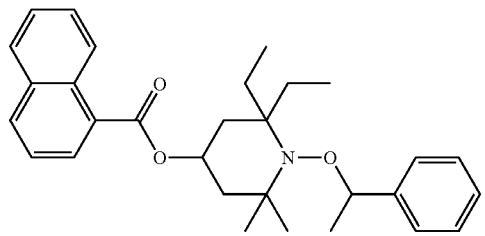

Naphthalene-1-carboxylic acid 2,2-diethyl-6,6-dimethyl-1-(1-phenyl-ethoxy)-piperidin-4-yl ester;

(42)

Ethyl-carbamic acid 2,2-diethyl-6,6-dimethyl-1-(1-phenyl-ethoxy)-piperidin-4-yl ester;

(38)

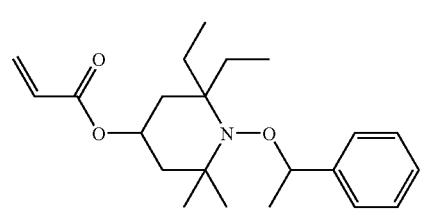

(43)

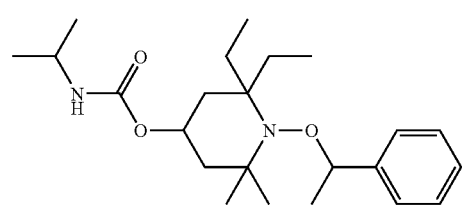

Isopropyl-carbamic acid 2,2-diethyl-6,6-dimethyl-1-(1-phenyl-ethoxy)-piperidin-4-yl ester;

p-Tolyl-carbamic acid 2,2-diethyl-6,6-dimethyl-1-(1-phenyl-ethoxy)-piperidin-4-yl ester;

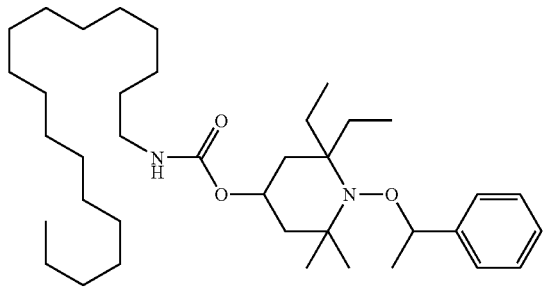

(44)

Octadecyl-carbamic acid 2,2-diethyl-6,6-dimethyl-1-(1-phenyl-ethoxy)-piperidin-4-yl ester;

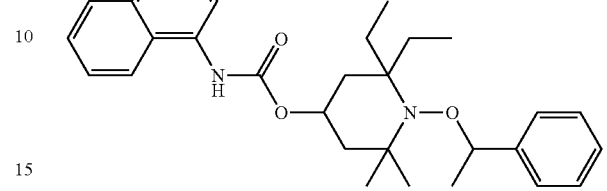

(48)

Naphthalen-1-yl-carbamic acid 2,2-diethyl-6,6-dimethyl-1-(1-phenyl-ethoxy)-piperidin-4-yl ester;

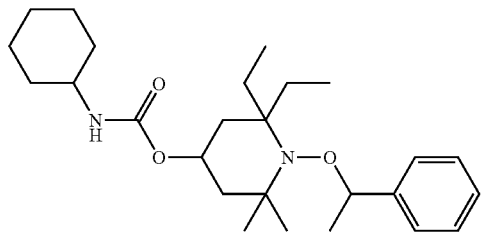

(45)

Cyclohexyl-carbamic acid 2,2-diethyl-6,6-dimethyl-1-(1-phenyl-ethoxy)-piperidin-4-yl ester;

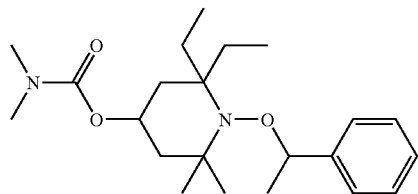

(49)

Dimethyl-carbamic acid 2,2-diethyl-6,6-dimethyl-1-(1-phenyl-ethoxy)-piperidin-4-yl ester;

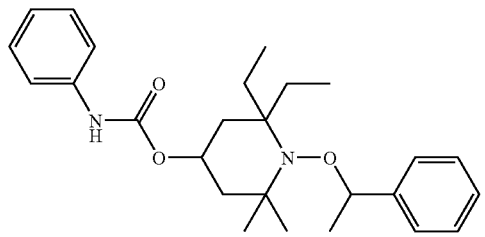

(46)

Cyclohexyl-carbamic acid 2,2-diethyl-6,6-dimethyl-1-(1-phenyl-ethoxy)-piperidin-4-yl ester;

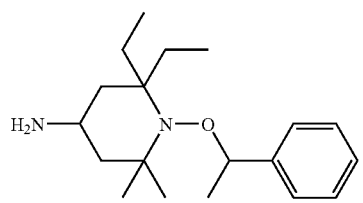

(50)

2,2-Diethyl-6,6-dimethyl-1-(1-phenyl-ethoxy)-piperidin-4-ylamine;

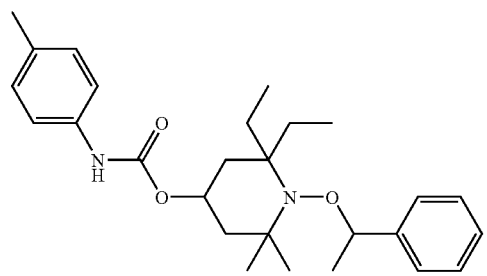

(47)

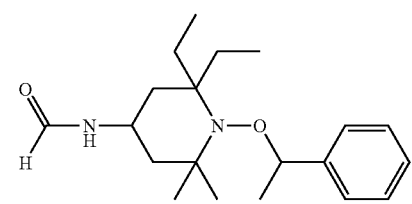

(51)

N-[2,2-Diethyl-6,6-dimethyl-1-(1-phenyl-ethoxy)-piperidin-4-yl]-formamide;

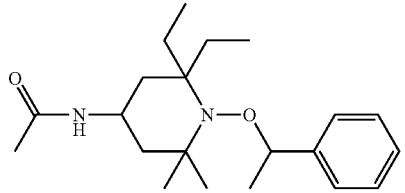

N-[2,2-Diethyl-6,6-dimethyl-1-(1-phenyl-ethoxy)-piperidin-4-yl]-acetamide;

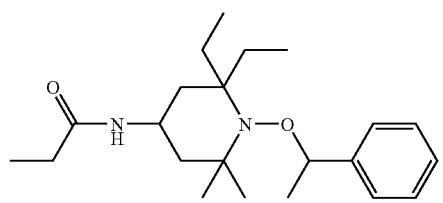

N-[2,2-Diethyl-6,6-dimethyl-1-(1-phenyl-ethoxy)-piperidin-4-yl]-propionamide;

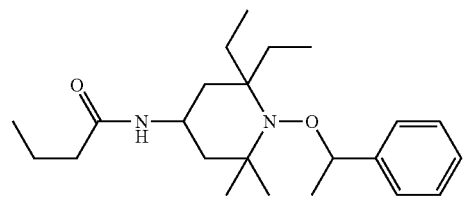

N-[2,2-Diethyl-6,6-dimethyl-1-(1-phenyl-ethoxy)-piperidin-4-yl]-butyramide;

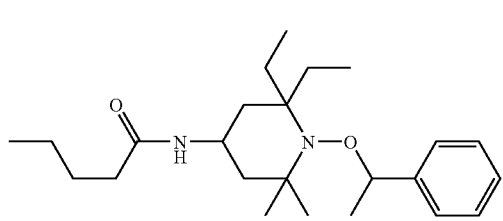

Pentanoic acid [2,2-diethyl-6,6-dimethyl-1-(1-phenyl-ethoxy)-piperidin-4-yl]-amide;

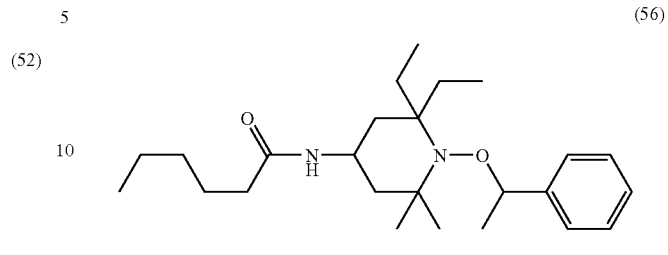

Hexanoic acid [2,2-diethyl-6,6-dimethyl-1-(1-phenyl-ethoxy)-piperidin-4-yl]-amide;

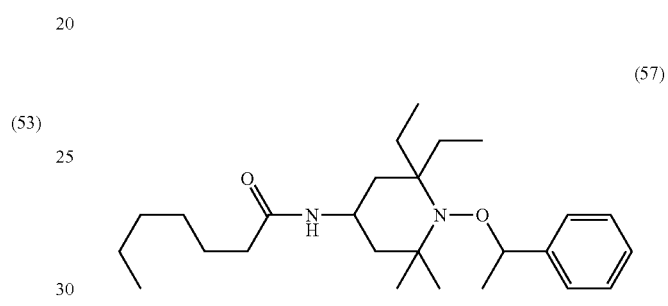

Heptanoic acid [2,2-diethyl-6,6-dimethyl-1-(1-phenyl-ethoxy)-piperidin-4-yl]-amide;

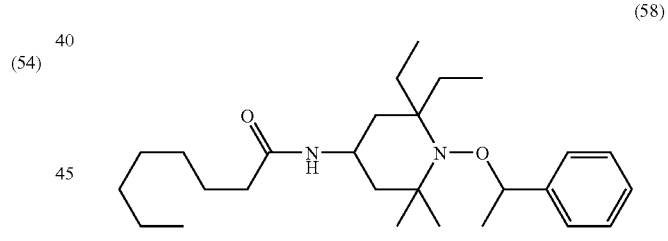

Octanoic acid [2,2-diethyl-6,6-dimethyl-1-(1-phenyl-ethoxy)-piperidin-4-yl]-amide;

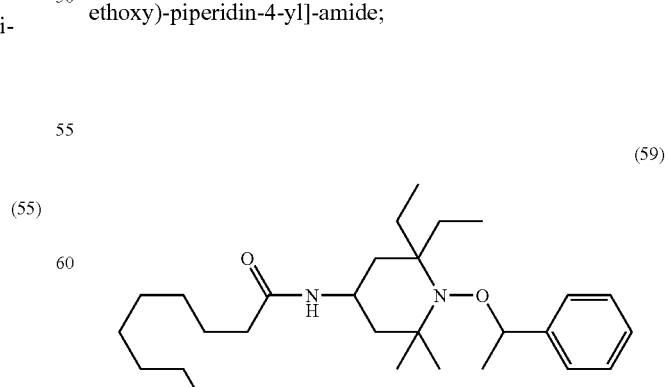

Nonanoic acid [2,2-diethyl-6,6-dimethyl-1-(1-phenyl-ethoxy)-piperidin-4-yl]-amide;

(60)

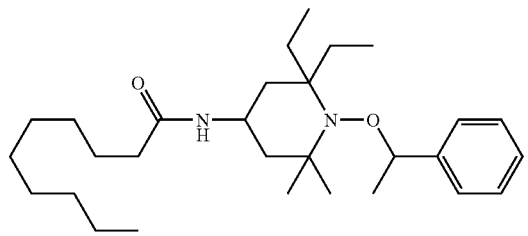

Decanoic acid [2-ethyl-2,6,6-trimethyl-1-(1-phenyl-ethoxy)-piperidin-4-yl]-amide;

(61)

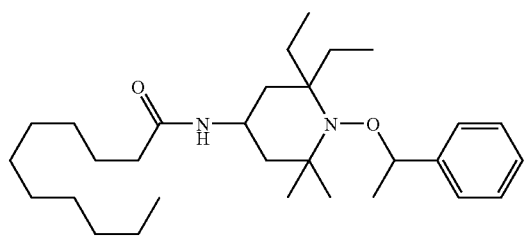

Undecanoic acid [2,2-diethyl-6,6-dimethyl-1-(1-phenyl-ethoxy)-piperidin-4-yl]-amide;

(62)

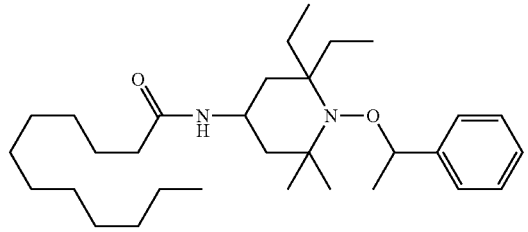

Dodecanoic acid [2,2-diethyl-6,6-dimethyl-1-(1-phenyl-ethoxy)-piperidin-4-yl]-amide;

(63)

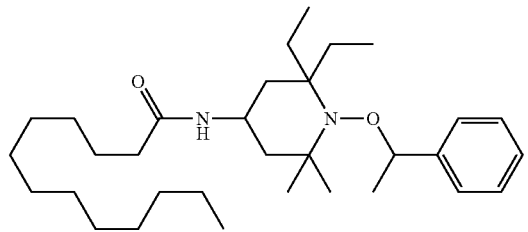

Tridecanoic acid [2,2-diethyl-6,6-dimethyl-1-(1-phenyl-ethoxy)-piperidin-4-yl]-amide;

(64)

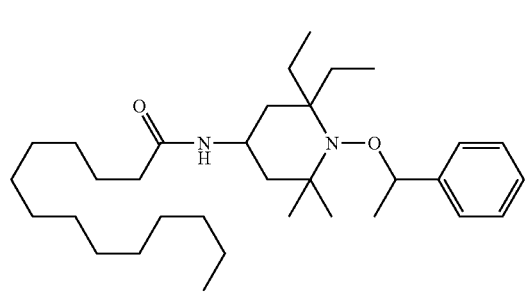

Tetradecanoic acid [2,2-diethyl-6,6-dimethyl-1-(1-phenyl-ethoxy)-piperidin-4-yl]-amide;

(65)

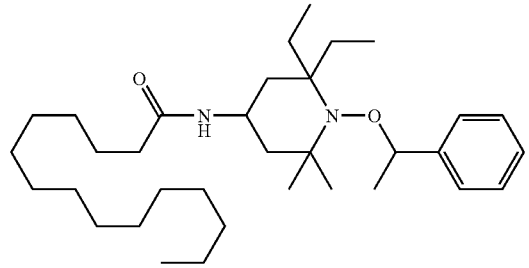

Pentadecanoic acid [2,2-diethyl-6,6-dimethyl-1-(1-phenyl-ethoxy)-piperidin-4-yl]-amide;

(66)

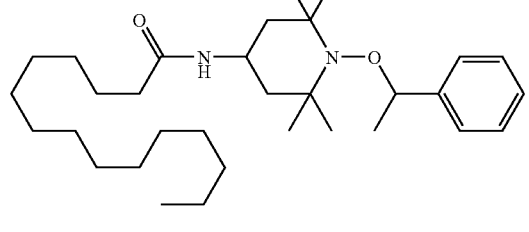

Pentadecanoic acid [2,2-diethyl-6,6-dimethyl-1-(1-phenyl-ethoxy)-piperidin-4-yl]-amide;

(67)

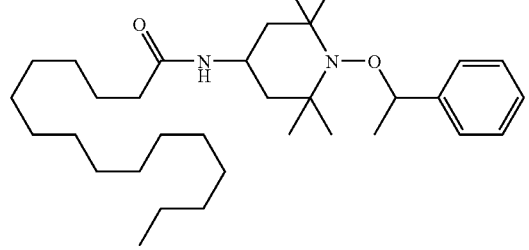

Hexadecanoic acid [2,2-diethyl-6,6-dimethyl-1-(1-phenyl-ethoxy)-piperidin-4-yl]-amide; (68)

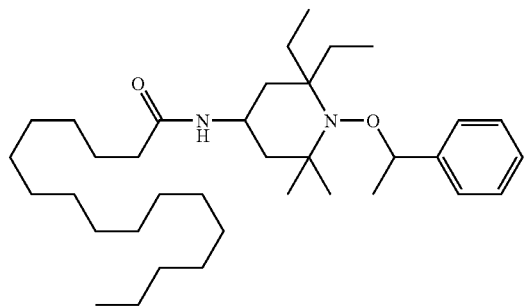

Heptadecanoic acid [2,2-diethyl-6,6-dimethyl-1-(1-phenyl-ethoxy)-piperidin-4-yl]-amide; (69)

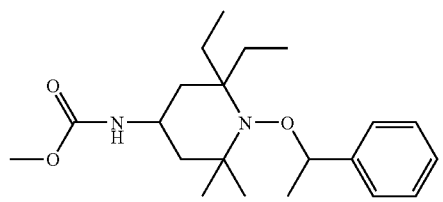

[2,2-Diethyl-6,6-dimethyl-1-(1-phenyl-ethoxy)-piperidin-4-yl]-carbamic acid methyl ester; (70)

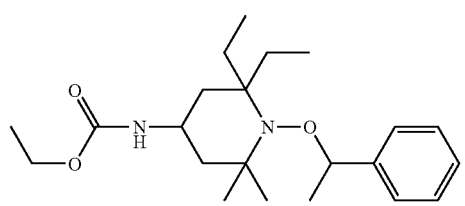

[2,2-Diethyl-6,6-dimethyl-1-(1-phenyl-ethoxy)-piperidin-4-yl]-carbamic acid ethyl ester; (71)

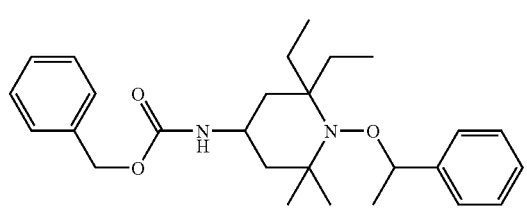

[2,2-Diethyl-6,6-dimethyl-1-(1-phenyl-ethoxy)-piperidin-4-yl]-carbamic acid benzyl ester; (72)

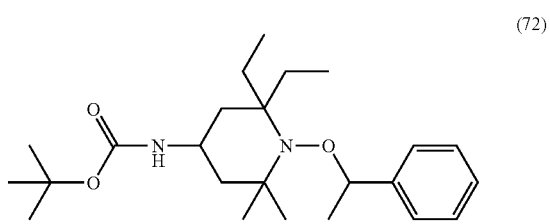

[2,2-Diethyl-6,6-dimethyl-1-(1-phenyl-ethoxy)-piperidin-4-yl]-carbamic acid .tert.-butyl ester; (73)

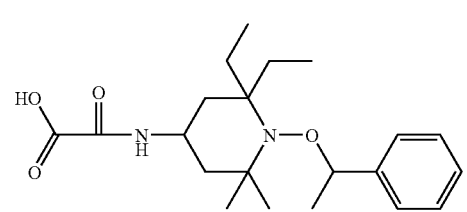

N-[2,2-Diethyl-6,6-dimethyl-1-(1-phenyl-ethoxy)-piperidin-4-yl]-oxalamic acid; (74)

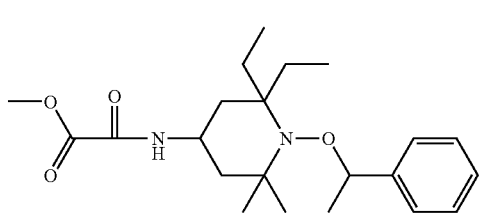

N-[2,2-Diethyl-6,6-dimethyl-1-(1-phenyl-ethoxy)-piperidin-4-yl]-oxalamic acid methyl ester; (75)

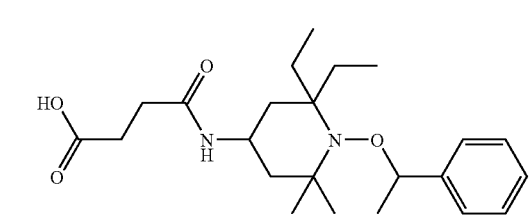

N-[2,2-Diethyl-6,6-dimethyl-1-(1-phenyl-ethoxy)-piperidin-4-yl]-succinamic acid;

4-[2,2-Diethyl-6,6-dimethyl-1-(1-phenyl-ethoxy)-piperidin-4-ylcarbamoyl]-butyric acid;

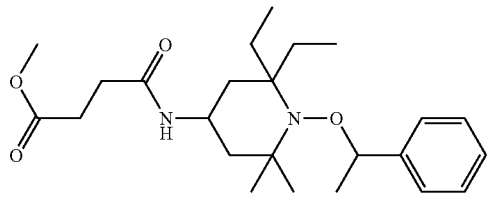
(76)

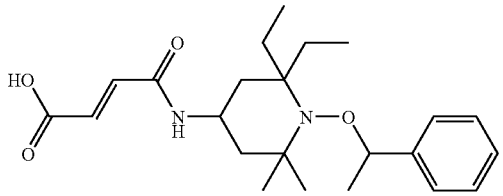
(80)

N-[2,2-Diethyl-6,6-dimethyl-1-(1-phenyl-ethoxy)-piperidin-4-yl]-succinamic acid methyl ester;

4-[2,2-Diethyl-6,6-dimethyl-1-(1-phenyl-ethoxy)-piperidin-4-ylcarbamoyl]-butyric acid methyl ester;

(77)

(81)

3-[2,2-Diethyl-6,6-dimethyl-1-(1-phenyl-ethoxy)-piperidin-4-ylcarbamoyl]-acrylic acid;

5-[2,2-Diethyl-6,6-dimethyl-1-(1-phenyl-ethoxy)-piperidin-4-ylcarbamoyl]-pentanoic acid;

(78)

(82)

3-[2,2-Diethyl-6,6-dimethyl-1-(1-phenyl-ethoxy)-piperidin-4-ylcarbamoyl]-acrylic acid methyl ester 5-[2,2-Diethyl-6,6-dimethyl-1-(1-phenyl-ethoxy)-piperidin-4-ylcarbamoyl]-pentanoic add methyl ester;

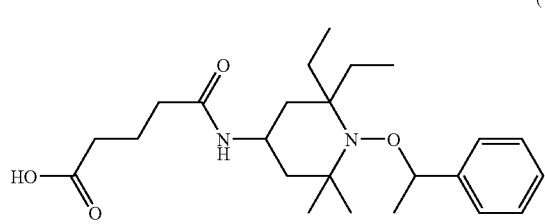
(79)

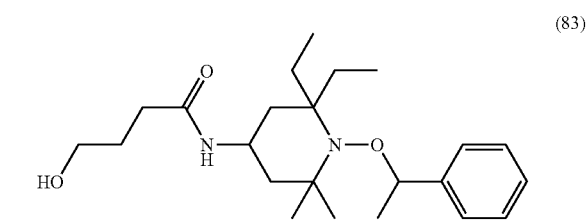
(83)

N-[2,2-Diethyl-6,6-dimethyl-1-(1-phenyl-ethoxy)-piperidin-4-yl]-4-hydroxy-butyramide;

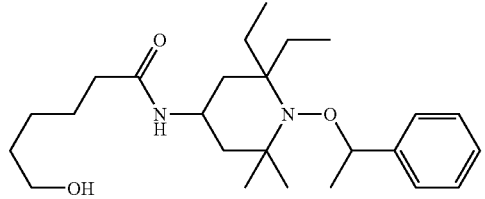

(84)

6-Hydroxy-hexanoic acid [2,2-diethyl-6,6-dimethyl-1-(1-phenyl-ethoxy)-piperidin-3-yl]-amide;

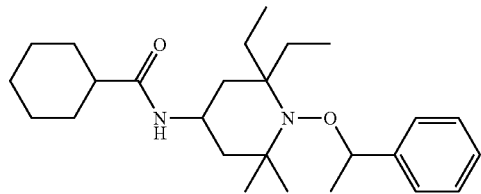

(85)

Cyclohexanecarboxylic acid [2,2-diethyl-6,6-dimethyl-1-(1-phenyl-ethoxy)-piperidin-4-yl]-amide;

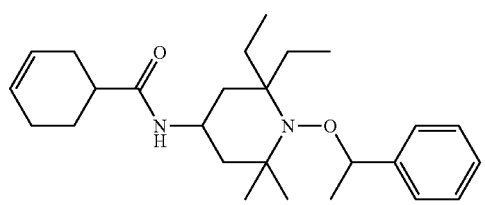

(86)

Cyclohex-3-enecarboxylic acid [22-diethyl-6,6-dimethyl-1-(1-phenyl-ethoxy)-piperidin-4-yl]-amide;

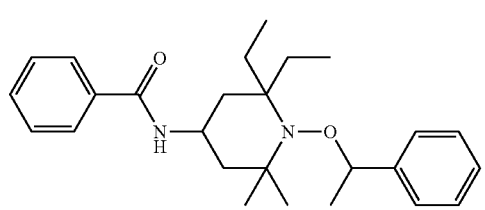

(87)

N-[2,2-Diethyl-6,6-dimethyl-1-(1-phenyl-ethoxy)-piperidin-4-yl]-benzamide;

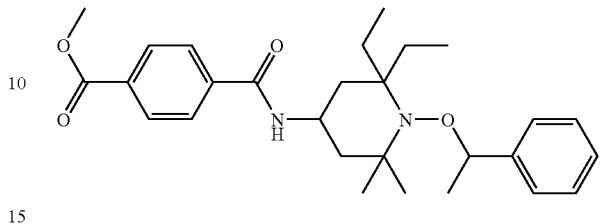

(88)

N-[2,2-Diethyl-6,6-dimethyl-1-(1-phenyl-ethoxy)-piperidin-4-yl]-terephthalamic acid methyl ester;

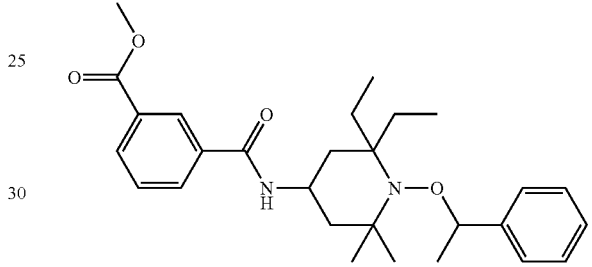

(89)

N-[2,2-Diethyl-6,6-dimethyl-1-(1-phenyl-ethoxy)-piperidin-4-yl]-isophthalamic acid methyl ester;

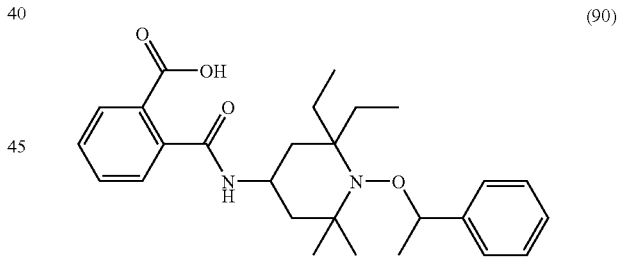

(90)

N-[2,2-Diethyl-6,6-dimethyl-1-(1-phenyl-ethoxy)-piperidin-4-yl]-phthalamic acid;

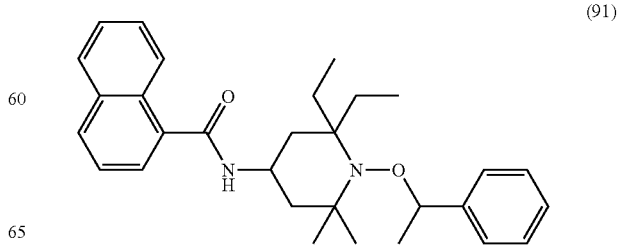

(91)

Naphthalene-1-carboxylic acid [2,2-diethyl-6,6-dimethyl-1-(1-phenyl-ethoxy)-piperidin-4-yl]-amide;

(92)

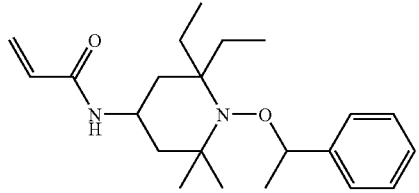

N-[2,2-Diethyl-6,6-dimethyl-1-(1-phenyl-ethoxy)-piperidin-4-yl]-acrylamide;

(93)

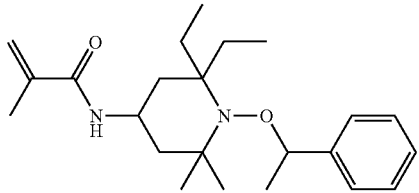

N-[2,2-Diethyl-6,6-dimethyl-1-(1-phenyl-ethoxy)-piperidin-4-yl]-2-methyl-acrylamide;

(94)

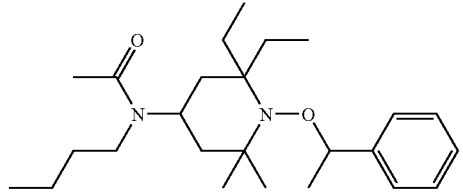

N-Butyl-.N.-[2,2-diethyl-6,6-dimethyl-1-(1-phenyl-ethoxy)-piperidin-4-yl]-acetamide (95)

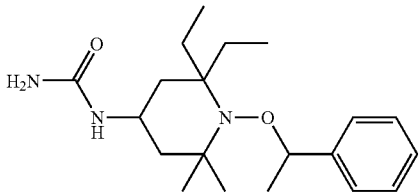

[2,2-Diethyl-6,6-dimethyl-1-(1-phenyl-ethoxy)-piperidin-4-yl]-urea;

(96)

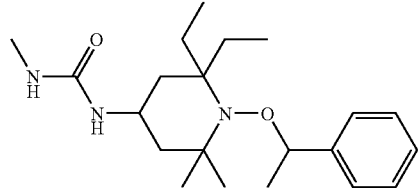

1-[2,2-Diethyl-6,6-dimethyl-1-(1-phenyl-ethoxy)-piperidin-4-yl]-3-methyl-urea;

(97)

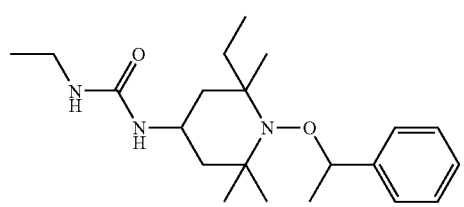

1-Ethyl-3-[2-ethyl-2,6,6-trimethyl-1-(1-phenyl-ethoxy)-piperidin-4-yl]-urea;

(98)

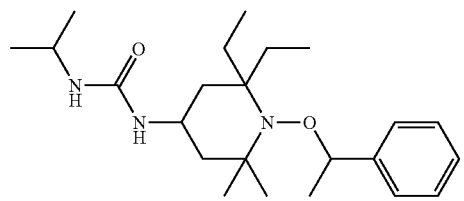

1-[2,2-Diethyl-6,6-dimethyl-1-(1-phenyl-ethoxy)-piperidin-4-yl]-3-isopropyl-urea;

(99)

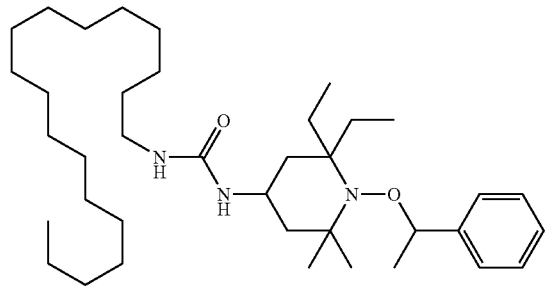

1-[2,2-Diethyl-6,6-dimethyl-1-(1-phenyl-ethoxy)-piperidin-4-yl]-3-octadecyl-urea;

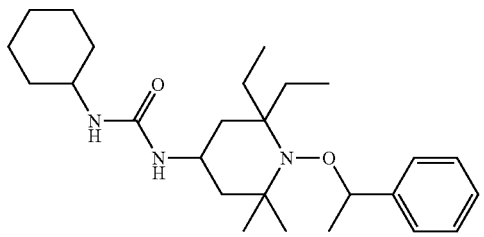
(100)

1-Cyclohexyl-3-[2,2-diethyl-6,6-dimethyl-1-(1-phenyl-ethoxy)-piperidin-4-yl]-urea;

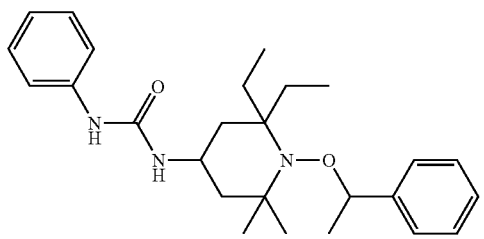
(101)

1-[2,2-Diethyl-6,6-dimethyl-1-(1-phenyl-ethoxy)-piperidin-4-yl]-4-phenyl-urea;

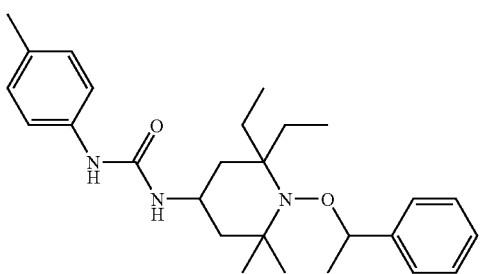
(102)

1-[2,2-Diethyl-6,6-dimethyl-1-(1-phenyl-ethoxy)-piperidin-4-yl]-3-.p.-tolyl-urea;

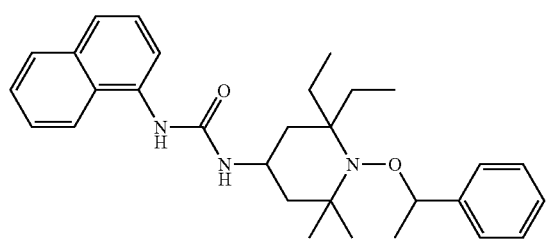
(103)

1-[2,2-Diethyl-6,6-dimethyl-1-(1-phenyl-ethoxy)-piperidin-4-yl]-3-naphthalen-1-yl-urea;

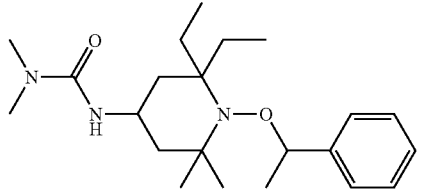
(104)

3-[2,2-Diethyl-6,6-dimethyl-1-(1-phenyl-ethoxy)-piperidin-4-yl]-1,1-dimethyl-urea;

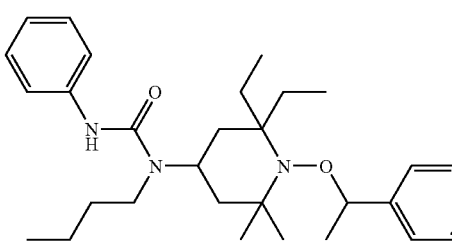
(105)

1-Butyl-1-[2,2-diethyl-6,6-dimethyl-1-(1-phenyl-ethoxy)-piperidin-4-yl]-3-phenyl-urea;

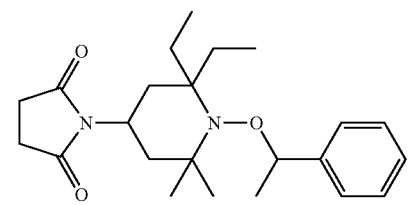
(106)

1-[2,2-Diethyl-6,6-dimethyl-1-(1-phenyl-ethoxy)-piperidin-4-yl]-pyrrolidine-2,5-dione;

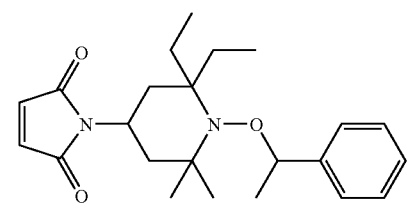
(107)

1-[2,2-Diethyl-6,6-dimethyl-1-(1-phenyl-ethoxy)-piperidin-4-yl]-pyrrole-2,5-dione;

(108)

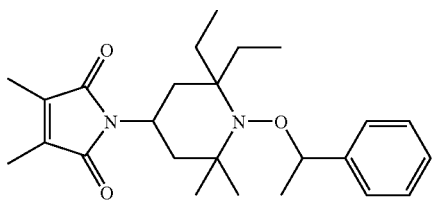

1-[2,2-Diethyl-6,6-dimethyl-1-(1-phenyl-ethoxy)-piperidin-4-yl]-3,4-dimethyl-pyrrole-2,5-dione;

(109)

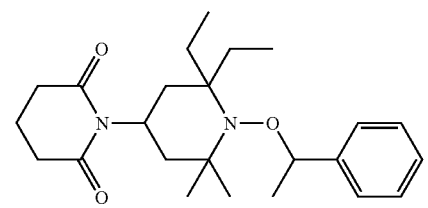

2',2'-Diethyl-6',6'-dimethyl-1'-(1-phenyl-ethoxy)-[1,4']bipiperidinyl-2,6-dione;

(110)

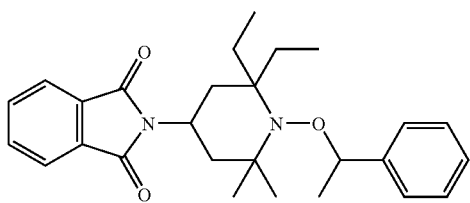

2-[2,2-Diethyl-6,6-dimethyl-1-(1-phenyl-ethoxy)-piperidin-4-yl]-isoindole-1,3-dione;

(111)

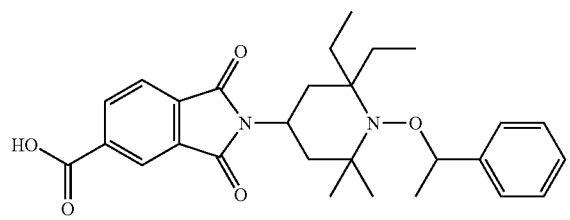

2-[2,2-Diethyl-6,6-dimethyl-1-(1-phenyl-ethoxy)-piperidin-4-yl]-1,3-dioxo-2,3-dihydro-1H-isoindole-5-carboxylic acid.

The compounds according to formulae Ia and IIa may be prepared according to standard methods.

The 4-OH intermediates are prepared as described in GB 2335190.

If Y is —C(O)—$R_1$ or C(O)—NH—$R_1$ the 4-OH intermediates are reacted with the desired carbonic acid derivatives or isocyanates according to the general scheme outlined below:

Most preferred are the following compounds.
(1) Formic acid 2,6-diethyl-2,3,6-trimethyl-1-(1-phenyl-ethoxy)-piperidin-4-yl ester;
(2) Acetic acid 2,6-diethyl-2,3,6-trimethyl-1-(1-phenyl-ethoxy)-piperidin-4-yl ester;
(3) Propionic acid 2,6-diethyl-2,3,6-trimethyl-1-(1-phenyl-ethoxy)-piperidin-4-yl ester;
(4) Butyric acid 2,6-diethyl-2,3,6-trimethyl-1-(1-phenyl-ethoxy)-piperidin-4-yl ester;
(5) Pentanoic acid 2,6-diethyl-2,3,6-trimethyl-1-(1-phenyl-ethoxy)-piperidin-4-yl ester;
(6) Hexanoic acid 2,6-diethyl-2,3,6-trimethyl-1-(1-phenyl-ethoxy)-piperidin-4-yl ester;
(7) Heptanoic acid 2,6-diethyl-2,3,6-trimethyl-1-(1-phenyl-ethoxy)-piperidin-4-yl ester;
(8) Octanoic acid 2,6-diethyl-2,3,6-trimethyl-1-(1-phenyl-ethoxy)-piperidin-4-yl ester;
(9) Nonanoic acid 2,6-diethyl-2,3,6-trimethyl-1-(1-phenyl-ethoxy)-piperidin-4-yl ester;
(10) Decanoic acid 2,6-diethyl-2,3,6-trimethyl-1-(1-phenyl-ethoxy)-piperidin-4-yl ester;
(11) Undecanoic acid 2,6-diethyl-2,3,6-trimethyl-1-(1-phenyl-ethoxy)-piperidin-4-yl ester;
(12) Dodecanoic acid 2,6-diethyl-2,3,6-trimethyl-1-(1-phenyl-ethoxy)-piperidin-4-yl ester;
(13) Tridecanoic acid 2,6-diethyl-2,3,6-trimethyl-1-(1-phenyl-ethoxy)-piperidin-4-yl ester;
(14) Tetradecanoic acid 2,6-diethyl-2,3,6-trimethyl-1-(1-phenyl-ethoxy)-piperidin-4-yl ester;
(15) Pentadecanoic acid 2,6-diethyl-2,3,6-trimethyl-1-(1-phenyl-ethoxy)-piperidin-4-yl ester;
(16) Hexadecanoic acid 2,6-diethyl-2,3,6-trimethyl-1-(1-phenyl-ethoxy)-piperidin-4-yl ester;
(17) Heptadecanoic acid 2,6-diethyl-2,3,6-trimethyl-1-(1-phenyl-ethoxy)-piperidin-4-yl ester;
(18) Octadecanoic acid 2,6-diethyl-2,3,6-trimethyl-1-(1-phenyl-ethoxy)-piperidin-4-yl ester;
(19) Formic acid 2,2-diethyl-6,6-dimethyl-1-(1-phenyl-ethoxy)-piperidin-4-yl ester;
(20) Acetic acid 2,2-diethyl-6,6-dimethyl-1-(1-phenyl-ethoxy)-piperidin-4-yl ester;
(21) Propionic acid 2,2-diethyl-6,6-dimethyl-1-(1-phenyl-ethoxy)-piperidin-4-yl ester;
(22) Butyric acid 2,2-diethyl-6,6-dimethyl-1-(1-phenyl-ethoxy)-piperidin-4-yl ester;
(23) Pentanoic acid 2,2-diethyl-6,6-dimethyl-1-(1-phenyl-ethoxy)-piperidin-4-yl ester;
(24) Hexanoic acid 2,2-diethyl-6,6-dimethyl-1-(1-phenyl-ethoxy)-piperidin-4-yl ester;
(25) Heptanoic acid 2,2-diethyl-6,6-dimethyl-1-(1-phenyl-ethoxy)-piperidin-4-yl ester;
(26) Octanoic acid 2,2-diethyl-6,6-dimethyl-1-(1-phenyl-ethoxy)-piperidin-4-yl ester;
(27) Nonanoic acid 2,2-diethyl-6,6-dimethyl-1-(1-phenyl-ethoxy)-piperidin-4-yl ester;
(28) Decanoic acid 2,2-diethyl-6,6-dimethyl-1-(1-phenyl-ethoxy)-piperidin-4-yl ester;
(29) Undecanoic acid 2,2-diethyl-6,6-dimethyl-1-(1-phenyl-ethoxy)-piperidin-4-yl ester;
(30) Dodecanoic acid 2,2-diethyl-6,6-dimethyl-1-(1-phenyl-ethoxy)-piperidin-4-yl ester;
(31) Tridecanoic acid 2,2-diethyl-6,6-dimethyl-1-(1-phenyl-ethoxy)-piperidin-4-yl ester;

(32) Tetradecanoic acid 2,2-diethyl-6,6-dimethyl-1-(1-phenyl-ethoxy)-piperidin-4-yl ester;

(33) Pentadecanoic acid 2,2-diethyl-6,6-dimethyl-1-(1-phenyl-ethoxy)-piperidin-4-yl ester;

(34) Hexadecanoic acid 2,2-diethyl-6,6-dimethyl-1-(1-phenyl-ethoxy)-piperidin-4-yl ester;

(35) Heptadecanoic acid 2,2-diethyl-6,6-dimethyl-1-(1-phenyl-ethoxy)-piperidin-4-yl ester;

(36) Octadecanoic acid 2,2-diethyl-6,6-dimethyl-1-(1-phenyl-ethoxy)-piperidin-4-yl ester;

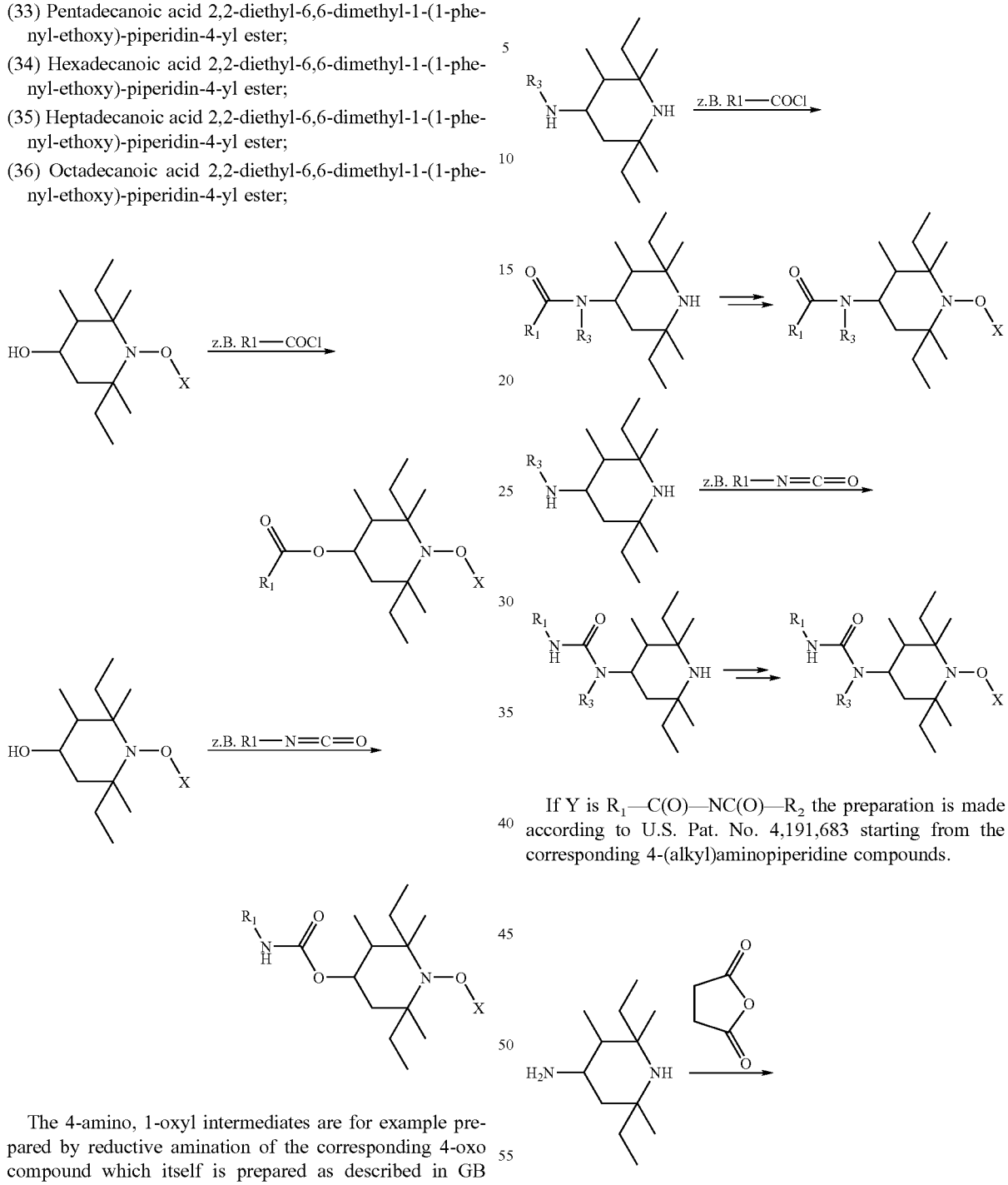

The 4-amino, 1-oxyl intermediates are for example prepared by reductive amination of the corresponding 4-oxo compound which itself is prepared as described in GB 2335190.

If Y is $-NR_3-C(O)-R_1$ or $-NR_3-C(O)-NHR_1$ the 4-amino or 4alkylamino compounds are reacted with carbonic acid derivatives (carbonic acid chloride, anhydride or ester) or isocynates. It is also possible to start from the corresponding piperidine compounds and to oxidize the intermediates to the corresponding N-oxides. This is for example described in U.S. Pat. No. 4,191,683. The nitroxides are then transformed into the corresponding alkoxyamines as described in GB 2335190.

This is schematically outlined below:

If Y is $R_1-C(O)-NC(O)-R_2$ the preparation is made according to U.S. Pat. No. 4,191,683 starting from the corresponding 4-(alkyl)aminopiperidine compounds.

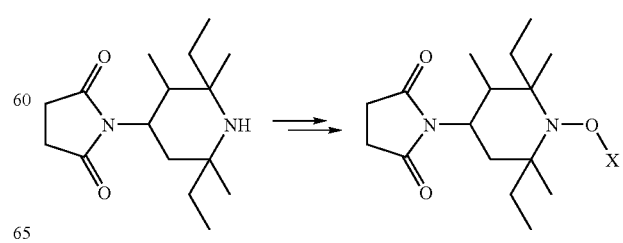

A further subject of the invention is a polymerizable composition, comprising a) at least one ethylenically unsaturated monomer or oligomer, and
b) a compound of formula Ia or IIa.

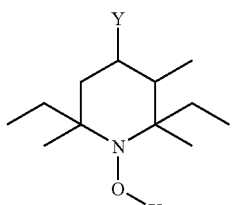
(Ia)

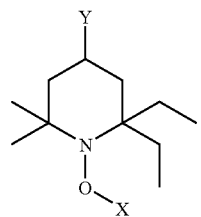
(IIa)

wherein

Y is a radical

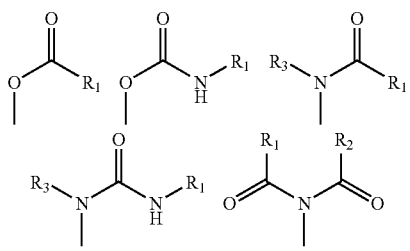

$R_1$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH, —COO($C_1$–$C_4$)alkyl, $C_2$–$C_{18}$alkyl which may be interrupted by one or more oxygen atom, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl)

$R_2$ is hydrogen, $C_1$–$C_{18}$alkyl or $R_1$ and $R_2$ together with the nitrogen atom form a 5-membered ring which may have an unsaturated bond or be fused to a benzene ring;

$R_3$ is hydrogen or $C_1$–$C_{18}$alky; and

X is selected from the group consisting of —($C_5$–$C_{12}$)-3-cycloalkenyl, —$CH_2$-phenyl; $CH_3CH$-phenyl, $(CH_3)_2C$-phenyl, $(C_5$–$C_6$cycloalkyl$)_2$CCN, $(CH_3)_2$CCN, —$CH_2CH$=$CH_2$, $CH_3CH$—CH=$CH_2$ ($C_1$–$C_4$alkyl)$CR_{20}$—C(O)-phenyl, ($C_1$–$C_4$)alkyl-$CR_{20}$—C(O)—($C_1$–$C_4$)alkoxy, ($C_1$–$C_4$)alkyl-$CR_{20}$—C(O)—($C_1$–$C_4$)alkyl, ($C_1$–$C_4$)alkyl-$CR_{20}$—C(O)—N-di($C_1$–$C_4$)alkyl, ($C_1$–$C_4$)alkyl-$CR_{20}$—C(O)—NH($C_1$–$C_4$)alkyl, ($C_1$–$C_4$)alkyl-$CR_{20}$—C(O)—$NH_2$, wherein $R_{20}$ is hydrogen or ($C_1$–$C_4$)alkyl.; with the proviso that benzoic acid 2,6-diethyl-2,3,6-trimethyl-1-(1-phenyl-ethoxy)-piperidin-4-yl ester is excluded.

Definitions for the substituents and preferred formulas have already been given. They apply also for the composition including the preferences.

Typically the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides or vinylidene halides.

Preferred ethylenically unsaturated monomers are ethylene, propylene, n-butylene, i-butylene, isoprene, 1,3-butadiene, α-$C_5$–$C_{18}$alkene, styrene, α-methyl styrene, p-methyl styrene or a compound of formula $CH_2$=C($R_a$)—(C=Z)-$R_b$, wherein $R_a$ is hydrogen or $C_1$–$C_4$alkyl, $R_b$ is $NH_2$, $O^-(Me^+)$, glycidyl, unsubstituted $C_1$–$C_{18}$alkoxy, $C_2$–$C_{100}$alkoxy interrupted by at least one N and/or O atom, or hydroxy-substituted $C_1$–$C_{18}$alkoxy, unsubstituted $C_1$–$C_{18}$alkylamino, di($C_1$–$C_{18}$alkyl)amino, hydroxy-substituted $C_1$–$C_{18}$alkylamino or hydroxy-substituted di($C_1$–$C_{18}$alkyl)amino, —O—$CH_2$—$CH_2$—N($CH_3$)$_2$ or —O—$CH_2$—$CH_2$—$N^+H(CH_3)_2$ $An^-$;

$An^-$ is a anion of a monovalent organic or inorganic acid;

Me is a monovalent metal atom or the ammonium ion.

Z is oxygen or sulfur.

Examples for $R_a$ as $C_2$–$C_{100}$alkoxy interrupted by at least one O atom are of formula

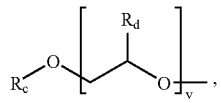

wherein $R_c$, is $C_1$–$C_{25}$alkyl, phenyl or phenyl substituted by $C_1$–$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

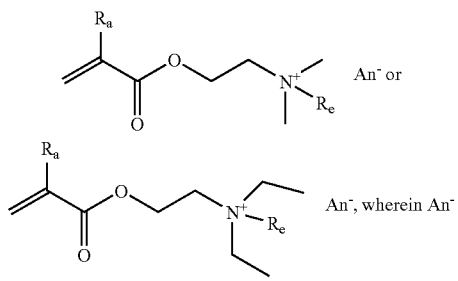

and $R_a$ have the meaning as defined above and $R_e$ is methyl or benzyl. $An^-$ is preferably $Cl^-$, $Br^-$ or $^-O_3S$—$CH_3$.

Further acrylate monomers are

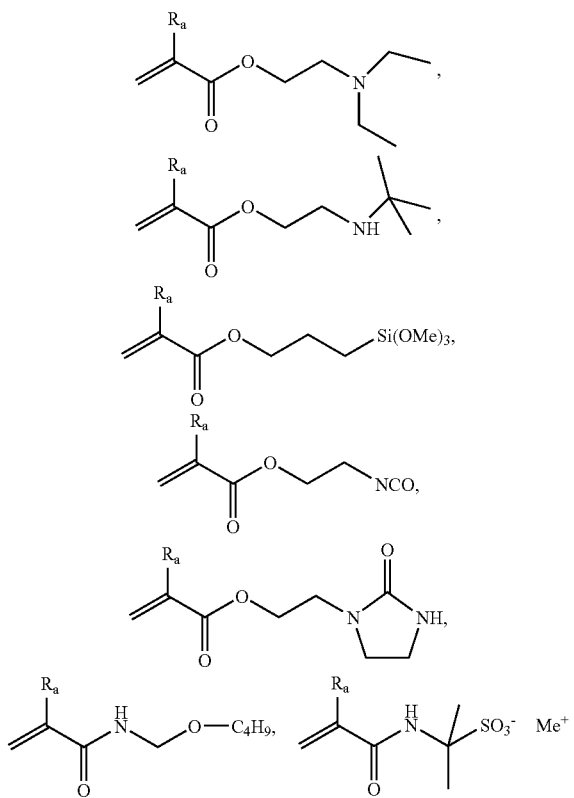

Examples for suitable monomers other than acrylates are

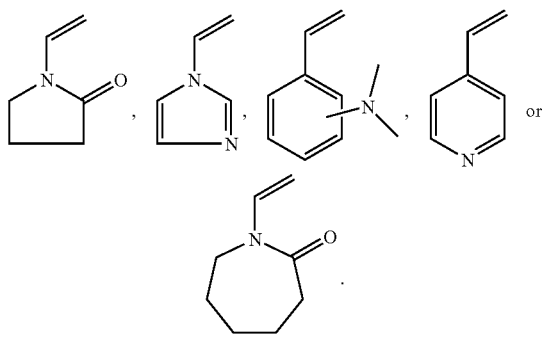

Preferably $R_a$ is hydrogen or methyl, $R_b$ is $NH_2$, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino; and Z is oxygen.

Particularly preferred ethylenically unsaturated monomers are styrene, methylacrylate, ethylacrylate, butylacrylate, isobutylacrylate, tert butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide, methacrylamide or dimethylaminopropyl-methacrylamide.

Preferably the initiator compound is present in an amount of from 0.01 mol-% to 30 mol-%, more preferably in an amount of from 0.1 mol-% to 20 mol-% and most preferred in an amount of from 0.1 mol-% to 10 mol-% based on the monomer or monomer mixture.

When monomer mixtures are used mol % is calculated on the average molecular weight of the mixture.

Another subject of the present invention is a process for preparing an oligomer, a cooligomer, a polymer or a copolymer (block or random) by free radical polymerization of at least one ethylenically unsaturated monomer or oligomer, which comprises (co)polymerizing the monomer or monomersoligomers in the presence of an initiator compound of formula Ia or IIa under reaction conditions capable of effecting scission of the O—C bond to form two free radicals, the radical ●X being capable of initiating polymerization.

Preferably scission of the O—C bond is effected by ultrasonic treatment, heating or exposure to electromagnetic radiation, ranging from γ to microwaves.

More preferably the scission of the O—C bond is effected by heating and takes place at a temperature of between 50° C. and 160° C.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosumides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The process is particularly useful for the preparation of block copolymers.

Block copolymers are, for example, block copolymers of polystyrene and polyacrylate (e.g., poly(styrene-co-acrylate) or poly(styrene-co-acrylatestyrene). They are usefull as adhesives or as compatibilizers for polymer blends or as polymer toughening agents. Poly(methylmethacrylate-co-acrylate) diblock copolymers or poly(methylacrylate-co-acrylate-co-methacrylate) triblock copolymers) are useful as dispersing agents for coating systeme, as coating additives (e.g. rheological agents, compatbilizers, reactive diluents) or as resin component in coatings(e.g. high solid paints) Block copolymers of styrene, (meth)acrylates and/or acrylonitrile are useful for plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1 000 to 400 000 g/mol, preferably from 2 000 to 250 000 g/mol and, more preferably, from 2 000 to 200 000 g/mol. When produced in bulk, the number average molecular weight may be up to 500 000 (with the same minimum weights as mentioned above). The number average molecular weight may be determined by size exclusion chromatography (SEC), gel permeation chromatography (GPC), matrix assisted laser desorption/ionization mass spectrometry (MALDI-MS) or, if the initiator carries a group which can be easily distinguished from the monomer(s), by NMR spectroscopy or other conventional methods.

The polymers or copolymers of the present invention have preferably a polydispersity of from 1.0 to 2, more preferably of from 1.1 to 1.9 and most preferably from 1.1 to 1.8.

Thus, the present invention also encompasses in the synthesis novel block, multi-block, star, gradient, random, hyperbranched and dendritic copolymers, as well as graft or copolymers.

The polymers prepared by the present invention are useful for following applications:

adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)-acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623–1627, dendrimers as described by K. Matyaszewski et al. in Macrmolecules 1996, Vol 29, No. 12, pages 4167–4171, graft (co)polymers as described by C. J. Hawker et al. in Macromol. Chem. Phys. 198, 155–166(1997), random copolymers as described by C. J. Hawker in Macromolecules 1996, 29, 2686–2688, or diblock and triblock copolymers as described by N. A. Listigovers in Macromolecules 1996, 29, 8992–8993.

A further subject of the present invention is a polymer or oligomer, having attached at least one initiator group —X and at least one oxyamine group of formula Ia or IIa.

The compounds of formula Ia and IIa may be prepared from the corresponding nitroxides, which are intermediates for the compounds of formula Ia and IIa.

Therefore still another subject of the present invention are nitroxides of formula IIIa and IVa.

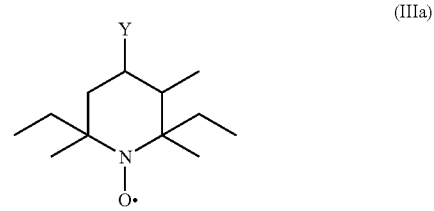

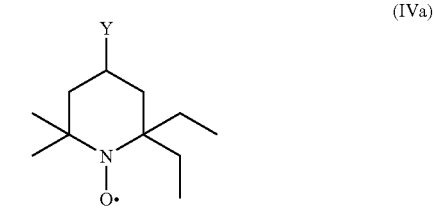

wherein
Y is a radical

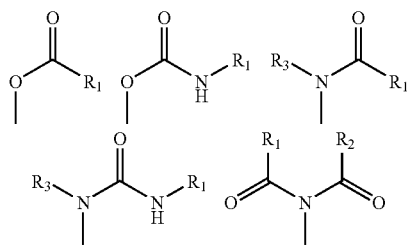

$R_1$ is hydrogen, —COOH, —COO($C_1$–$C_4$alkyl), —COOphenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH, —COO($C_1$–$C_4$)alkyl, $C_2$–$C_{18}$alkyl which may be interrupted by one or more oxygen atom, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl)

$R_2$ is hydrogen, $C_1$–$C_{18}$alkyl or $R_1$ and $R_2$ together with the nitrogen atom form a 5-membered ring which may have an unsaturated bond or be fused to a benzene ring;

$R_3$ is hydrogen or $C_1$–$C_{18}$alky; with the proviso that 2,6-diethyl-2,3,6-trimethyl-4-lauroyloxypiperidine-1-oxyl, 2,6-diethyl-2,3,6-trimethyl-4-stearoyloxypiperidine-1-oxyl, 2,2-dimethyl-6,6-diethyl-4-lauroyloxypiperidine-1-oxyl and 2,2-dimethyl-6,6-diethyl-4-stearoyloxypiperidine-1-oxyl are excluded.

Definitions for the substituents as well as their preferences have already been given. They apply also for the compounds of formula IIIa and IVa.

Particular preference is given to the individual compounds according to formulae Ia and IIa, given above, for which the corresponding N-oxides are precursors, which are therefore also of particular interest.

The compounds of formula IIIa and IVa are also particularly useful for controlled polymerization reactions in combination with a source of free radicals.

Also subject of the present invention is a polymerizable composition, comprising
 a) at least one ethylenically unsaturated monomer or oligomer, and
 b) a compound of formula IIIa or IVa and
 c) a source of free radicals capable of initiating polymerization of ethylenically unsaturated monomers.

The production of C-centered radicals is described, inter alia, in Houben Weyl, Methoden der Organischen Chemie, Vol. E 19a, pages 60–147. These methods can be applied in general analogy.

The source of radicals may be a bis-azo compound, a peroxide or a hydroperoxide.

Preferably, the source of radicals is 2,2'-azobisisobutyronitrile, 2,2'-azobis(2-methyl-butyronitrile), 2,2'-azobis(2,4-dimethylvaleronitrile), 2,2'-azobis(4-methoxy-2,4-dimethylvaleronitrile), 1,1'-azobis(1-cyclohexanecarbonitrile), 2,2'-azobis(isobutyramide)dehydrate, 2-phenylazo-2,4-dimethyl-4-methoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} or 2,2'-azobis(2-methyl-N-[1,1-bis(hydroxymethyl)-2-hydroxyethyl]propionamide.

Preferred peroxides and hydroperoxides are acetyl cyclohexane sulphonyl peroxide, diisopropyl peroxy dicarbonate, t-amyl pemeodecanoate, t-butyl pemeodecanoate, t-butyl perpivalate, t-amylperpivalate, bis(2,4-dichlorobenzoyl)peroxide, diisononanoyl peroxide, didecanoyl peroxide, dioctanoyl peroxide, dilauroyl peroxide, bis(2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)3,5,5-trimethylcyclohexane, 1,1-bis(t-butylperoxy)cyclohexane, t-butyl peroxy isopropyl carbonate, t-butyl perisononaoate, 2,5-dimethylhexane 2,5-dibenzoate, t-butyl peracetate, t-amyl perbenzoate, t-butyl perbenzoate, 2,2-bis(t-butylperoxy)butane, 2,2 bis(t-butylperoxy)propane, dicumyl peroxide, 2,5-dimethylhexane-2,5-di-t-butylperoxide, 3-t-butylperoxy 3-phenylphthalide, di-t-amyl peroxide, α,α'-bis(t-butylperoxy isopropyl)benzene, 3,5-bis(t-butylperoxy)3,5-dimethyl 1,2-dioxolane, di-t-butyl peroxide, 2,5-dimethylhexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

These compounds are commercially available.

If more than one radical source is used, a mixture of substitution patterns is obtainable.

The radical source is preferably present in an amount of from 0.01 mol-% to 30 mol-%, more preferred in an amount of from 0.1 mol-% to 20 mol-% and most preferred in an amount of from 0.5 mol-% to 10 mol-% based on the monomer or monomer mixture.

The molar ratio of the radical source to the compound of formulae II may be from 1:10 to 10:1, preferably from 1:5 to 5:1 and more preferably from 1:2 to 2:1.

Still another subject of the present invention is a process for preparing an oligomer, a cooligomer, a polymer or a copolymer (block or random) by free radical polymerization of at least one ethylenically unsaturated monomer/oligomer, which comprises subjecting the above composition to heat or actinic radiation.

Further subjects of the invention is the use of a compound of formulae Ia or IIa

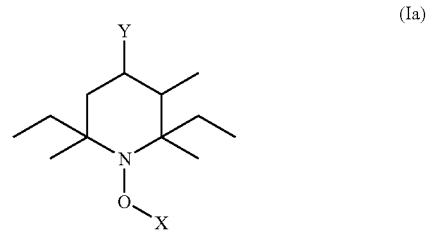

(Ia)

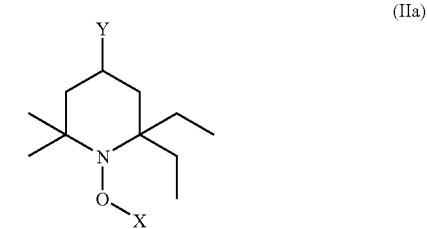

(IIa)

for the polymerization of ethylenically unsaturated monomers and the use of of a compound of formulae IIIa or IVa

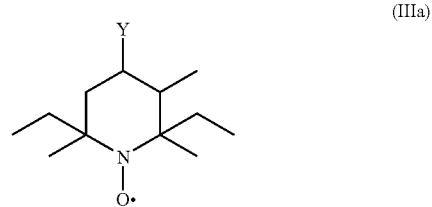

(IIIa)

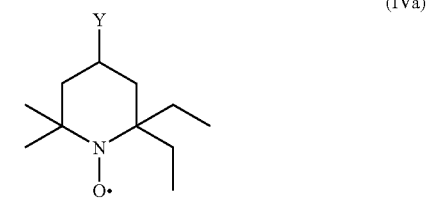

(IVa)

together with a source of free radicals for the polymerization of an ethylenically unsaturated monomer.

Definitions and preferences for the various substituents have already been mentioned with respect to the initiator compounds. They apply also for the other subjects of the invention including the preferences and the individual compounds.

The following examples illustrate the invention.

EXAMPLE A1

Acetic acid 2,6-diethyl-2,3,6-trimethyl-1-(1-phenyl-ethoxy)-piperidin-4-yl ester (Formula Ia, Compound 2)

To a solution of 6.36 g (2 mmol) of 2,6-diethyl-2,3,6-trimethyl-1-(1-phenyl-ethoxy)-piperidin-4-ol (prepared as described in GB 2335190, example 7, compound 102) and 2.02 g (2 mmol) of triethylamine in 50 ml toluene are added 1.57 g (2 mmol) acetyl chloride at 0–5° C. and the reaction mixture is stirred for 2 hours at 20° C. The reaction mixture is then several times extracted with water. The organic phase is dried over $Na_2SO_4$ and after removing the solvent 6.9 g (96%) acetic acid 2,6-diethyl-2,3,6-trimethyl-1-(1-phenyl-ethoxy)-piperidin-4-yl ester are obtained as yellowish liquid.

Elemental analysis calculated for $C_{22}H_{35}NO_3$: C, 73.0%; H, 9.76%; N, 3.87%. Found: C, 72.87%; H, 9.64%; N, 3.85%.

EXAMPLE A2

Acrylic acid 2,6-diethyl-2,3,6-trimethyl-1-(1-phenyl-ethoxy)-piperidin-4-yl ester (Formula Ia, Compound 39)

In analogy to example 1 were reacted 6.36 g (2 mmol) of 2,6-diethyl-2,3,6-trimethyl-1-(1-phenyl-ethoxy)-piperidin-4-ol with 1.81 g (2 mmol) of acryloyl chloride and 2.02 g (2 mmol) of triethylamine in toluene to give 6.5 g (87%) acrylic acid 2,6-di-ethyl-2,3,6-trimethyl-1-(1-phenyl-ethoxy)-piperidin-4-yl ester as yellowish liquid.

Elemental analysis calculated for $C_{23}H_{35}NO_3$: C, 73.95%; H, 9.44%; N, 3.75%. Found: C, 74.43%; H, 9.44%; N, 3.91%.

EXAMPLE A3

Dodecanoic acid 2,6-diethyl-2,3,6-trimethyl-1-(1-phenyl-ethoxy)-piperidin-4-yl ester (Formula Ia, Compound 12)

In analogy to example 1 were reacted 6.36 g (2 mmol) of 2,6-diethyl-2,3,6-trimethyl-1-(1-phenyl-ethoxy)-piperidin-4-ol with 4.38 g (2 mmol) of lauroyl chloride and 2.02 g (2 mmol) of triethylamine in toluene to give 9.4 g (94%) dodecanoic acid 2,6-diethyl-2,3,6-trimethyl-1-(1-phenyl-ethoxy)-piperidin-4-yl ester as yellowish liquid.

Elemental analysis calculated for $C_{32}H_{55}NO_3$: C, 76.59%; H, 11.05%; N, 2.79%. Found: C, 76.17%; H, 11.75%; N, 2.69%.

EXAMPLE A4

Dodecanoic acid 2,2-diethyl-6,6-dimethyl-1-(1-phenyl-ethoxy)-piperidin-4-yl ester (Formula IIa, Compound 12)

In analogy to example 1 were reacted 6.1 g (2 mmol) of 2,2-diethyl-6,6-dimethyl-1-(1-phenyl-ethoxy)-piperidin-4-ol (prepared as described in GB 2335190, compound 110) with 4.38 g (2 mmol) of lauroyl chloride chloride and 2.02 g (2 mmol) of triethylamine in toluene to give 8.9 g (91%) dodecanoic acid 2,2-diethyl-6,6-dimethyl-1-(1-phenyl-ethoxy)-piperidin-4-yl ester as yellowish liquid.

Elemental analysis calculated for $C_{31}H_{53}NO_3$: C, 76.33%; H, 10.95%; N, 2.87%. Found: C, 75.57%; H, 10.92%; N, 2.90%.

EXAMPLE A5

(N-[2,6-Diethyl-2,3,6-trimethyl-1-(1-phenyl-ethoxy)-piperidin-4-yl]-benzamide (Formula Ia, Compound 88)

A) N-[2,6-Diethyl-2,3,6-trimethyl-piperidin-1-oxyl-4-yl]-benzamide

To a solution of 30.2 g (0.1 mol) N-[2,6-diethyl-2,3,6-trimethyl-piperidine-4-yl]-benzamide (prepared according to U.S. Pat. No. 4,191,683) in 100 ml ethylacetate, 38 g (0.2 mol) 40% peracetic acid in acetic acid are dropwise added under cooling with ice. The mixture is stirred for 12 hours at room temperature. The red solution is washed with water, then with 5% solution of NaOH and again with water, dried over $MgSO_4$ and concentrated under vacuum. 31.2 g (98%) N-[2,6-Diethyl-2,3,6-trimethyl-piperidin-1-oxyl-4-yl]-benzamide as an amorphous solid are obtained.

B) In a photo reactor 150 ml ethylbenzene, 6.35 g (0,02 mol) N-[2,6-diethyl-2,3,6-trimethyl-piperidin-1-oxyl-4-yl]-benzamide and 12.7 g (0,087 mol) t-butylperoxide are added. The red solution is purged with nitrogen and subsequently irradiated with a mercury lamp under nitrogen atmosphere at 20–25° C. (pyrex glas). After 8 hours the solution has become colorless. The reaction mixture is concentrated under vaccum. The residue is purified by chromatography on silicagel with hexane-ethylacetate (9:1) and crystallized from hexane-toluene. 2.53 g (30%) of a colourless solid are obtained mp. 112–147° C.

$^1$H-NMR (300 MHz, $CDCl_3$): 8.0–7.13 (m, 10 ArH), 6.0–5.85 (m, 1H), 4.8–4.65 (m, 1H), 4.65–4.40 (m, 1H), 2.40–0.5 (m, 25H).

EXAMPLE A6

1-[2,6-Diethyl-2,3,6-trimethyl-1-(1-phenyl-ethoxy)-piperidin-4-yl]-3-ethyl-urea (Formula Ia, Compound 98)

A) 1-[2,6-Diethyl-2,3,6-trimethyl-piperidin-1-oxyl-4-yl]-3-ethyl-urea

To a solution of 19.8 g (0.1 mol) 2,6-diethyl-2,3,6-trimethyl-piperidin-4-yl-amine (prepared according to U.S. Pat. No. 4,191,683) in 30 ml toluene, 7.1 g (0.1 mol) ethylisocyanate are dropwise added. The mixture is stirred for 5 hours at room temperature and subsequently concentrated under vaccum. The residue is dissolved in 60 ml ethylacetate and peracefic acid 40% are added slowly under cooling with ice water. The mixture is stirred for another 15 hours at room temperature. The red solution is washed with water, then with 5% solution of NaOH and again with water, dried over $MgSO_4$ and concentrated under vacuum. 25.65 g (90%) 1-[2,6-Diethyl-2,3,6-trimethyl-piperidin-1-oxyl-4-yl]-3-ethyl-urea are obtained as a resinous material.

B) 1.08 g (0.038 mol) 1-[2,6-Diethyl-2,3,6-trimethyl-piperidin-1-oxyl-4-yl]-3-ethyl-urea are reacted in analogy to example 5 with ethylbenzene and di-t-butylperoxide. After chromatographic purification on silicagel hexane-ethylacete (3:2) 0.7 g (47%) 1-[2,6-diethyl-2,3,6-trimethyl-1-(1-phenyl-ethoxy)-piperidin-4-yl]-3-ethyl-urea are obtained as a colorless solid.

$^1$H-NMR (300 MHz, $CDCl_3$): 7.4–5.2 (m, 5H), 4.8–4.6 (m, 1H), 4.5–3.9 (m, 3H), 3.3–3.1 (m 2H), 2.3–0.4 (m, 18H).

EXAMPLE A7

2-[2,6-Diethyl-2,3,6-trimethyl-1-(1-phenyl-ethoxy)-piperidin-4-yl]-isoindole-1,3-dione (Formula Ia, Compound 111)

A) 2-[2,6-Diethyl-2,3,6-trimethyl-piperidin-1-oxyl-4-yl]-isoindole-1,3-dione

To a solution of 16.4 g (0.05 mol) 2-[2,6-diethyl-2,3,6-trimethyl-piperidin-4-yl]-isoindole-1,3-dione (prepared according to U.S. Pat. No. 4,191,683) in 50 ml 1,2-dichlorobenzene 20.6 g (0.1 mol) peracetic acid 40% in acetic acid are dropwise added under cooling with ice. The mixture is stirred for 66 hours at room temperature. The red solution is washed with water, then with 5% solution of NaOH and again with water, dried over $MgSO_4$ and concentrated under vacuum. 16.28 g (95%) 2-[2,6-diethyl-2,3,6-trimethyl-piperidin-1-oxyl-4-yl]-isoindole-1,3-dione are obtained as an amorphous solid.

B) 1.54 g (0.0044 mol) 2-[2,6-diethyl-2,3,6-trimethyl-piperidin-1-oxyl-4-yl]-isoindole-1,3-dione are reacted in analogy to example 5 with ethylbenzene and di-t-butylperoxide. After chromatographic purification on silicagel with hexane-ethylacete (14:1) 1.63 g (84%) 2-[2,6-Diethyl-2,3,6-trimethyl-1-(1-phenyl-ethoxy)-piperidin-4-yl]-isoindole-1,3-dione are obtained as a colourless amorpous solid.

$^1$H-NMR (300 MHz, $CDCl_3$): 7.8–7.1 (m, 9H), 4.9–4.5 (m, 1H), 3.3–0.5 (m, 26H).

B) Polymerizations using compounds of formulae Ia or IIa initiators/regulators

General Remarks:

Solvents and monomers are distilled over a Vigreux column under argon atmosphere or under vacuum, shortly before being used.

To remove oxygen all polymerization reaction mixtures are flushed before polymerization with argon and evacuated under vaccum applying a freeze-thaw cycle. The reaction mixtures are then polymerized under argon atmosphere.

At the start of the polymerization reaction, all starting materials are homogeneously dissolved.

Conversion is determined by removing unreacted monomers from the polymer at 80° C. and 0.002 torr for 30 minutes, weighing the remaining polymer and subtract the weight of the initiator.

GPC: Is performed using RHEOS 4000 of FLUX INSTRUMENTS. Tetrahydrofurane (THF) is used as a solvent and is pumped at 1 ml/min. Two chromatography columns are put in series: type Plgel 5 µm mixed-C of POLYMER INSTRUMENTS, Shropshire, UK. Measurements are performed at 40° C. The columns are calibrated with low polydispersity polystyrenes having Mn from 200 to 2 000 000 Dalton. Detection is carried out using a RI-Detector ERC-7515A of ERCATECH AG at 30° C.

EXAMPLE B1

Polymerization of n-butylacrylate Using 1.5 mol % of Compound 2 of Formula Ia (Example A1) at 145° C.

In a 50 ml three neck flask, equipped with thermometer, cooler and magnetic stirrer, 338 mg (0.94 mmol) of compound 2 and 8 g (62.4 mmol) of n-butylacrylate are mixed and degased. The clear solution obtained is heated under argon to 145° C. and polymerization is carried out during 5 h. The reaction mixture is then cooled to 70° C. The remaining monomer is removed by evaporation under high vacuum. 6.64 g (83%) of the initial monomer have reacted. A clear colorless viscous fluid is obtained.

Mn=6700, Mw=8700, PD=1.3

EXAMPLE B2

Polymerization of n-butylacrylate Using 1.5 mol % of Compound 2 of Formula Ia (Example A1) at 130° C.

In a 50 ml three neck flask, equipped with thermometer, cooler and magnetic stirrer, 338 mg (0.94 mmol) of compound 2 and 8 g (62.4 mmol) of n-butylacrylate are mixed and degased. The clear solution obtained is heated under argon to 130° C. and polymerization is carried out during 5 h. The reaction mixture is then cooled to 70° C. The remaining monomer is removed by evaporation under high vacuum. 4.16 g (52%) of the initial monomer have reacted. A clear colorless viscous fluid is obtained.

Mn=4300, Mw=5200, PD=1.2

EXAMPLE B3

Polymerization of n-butylacrylate Using 1.2 mol % of Compound 2 of Formula Ia (Example A1) at 145° C.

In a 50 ml three neck flask, equipped with thermometer, cooler and magnetic stirrer, 338 mg (0.94 mmol) of compound 2 and 10 g (78 mmol) of n-butylacrylate are mixed and degased. The clear solution obtained is heated under argon to 145° C. and polymerization is carried out during 5 h. The reaction mixture is then cooled to 70° C. The remaining monomer is removed by evaporation under high vacuum. 8 g (80%) of the initial monomer have reacted. A clear colorless viscous fluid is obtained.

Mn=8500, Mw=11000, PD=1.3

EXAMPLE B4

Copolymerisation of poly(n-butylacrylat) with N,N-dimethylaminoethylacrylat (DMAEA)

In a 50 ml three neck flask, equipped with thermometer, cooler and magnetic stirrer 6 g of poly(n-butylacrylates) of example B3 and 6 g (42 mmol) N,N-dimethylaminoethylacrylat are mixed and degassed. The clear solution obtained is heated under argon to 145° C. and polymerization is carried out during 3.5 h. The remaining monomer is removed by evaporation under high vacuum. 2.4 g (40%) of the initial monomer have reacted. A clear orange viscous fluid is obtained.

Composition (NMR): 65 weight % butylacrylat/35 weight % N,N-dimethylaminoethylacrylat
Mn=13000, Mw=22150, PD=1.7

The invention claimed is:
1. A polymerizable composition comprising
   a) at least one ethylenically unsaturated monomer or oligomer,
   b) a compound of formula IIIa or IVa and
   c) a source of free radicals capable of initiating polymerization of ethylenically unsaturated monomers,
wherein the compounds of formula IIIa and IVa are

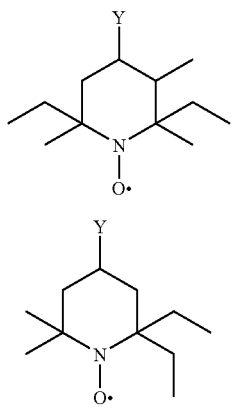

(IIIa)

(IVa)

wherein
Y is selected from the group consisting of

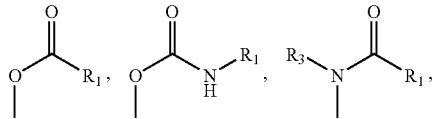

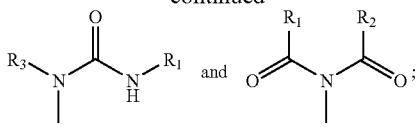

and $R_1$ is hydrogen, —COOH, —COO($C_1$–$C_4$alkyl), —COO-phenyl, —COObenzyl, $C_1$–$C_8$alkoxy, $C_1$–$C_{18}$alkyl, $C_2$–$C_4$alkenyl, $C_1$–$C_{18}$alkyl or $C_2$–$C_4$alkenyl substituted by OH, —COOH, —COO($C_1$–$C_4$)alkyl, $C_2$–$C_{18}$alkyl which may be interrupted by one or more oxygen atom, unsubstituted cyclopentyl, cyclohexyl, cyclohexenyl, phenyl or naphthyl; or cyclopentyl, cyclohexyl, cylohexenyl, phenyl or naphthyl which are substituted by $C_1$–$C_4$alkyl, —COOH or —COO—($C_1$–$C_4$alkyl);

$R_2$ is hydrogen, $C_1$–$C_{18}$alkyl or $R_1$ and $R_2$ together with the nitrogen atom form a 5-membered ring which may have an unsaturated bond or be fused to a benzene ring; and $R_3$ is hydrogen or $C_1$–$C_{18}$alkyl;

with the proviso that
2,6-diethyl-2,3,6-trimethyl-4-lauroyloxypiperidine-1-oxyl,
2,6-diethyl-2,3,6-trimethyl-4-stearoyloxypiperidine-1-oxyl,
2,2-dimethyl-6,6-diethyl-4-lauroyloxypiperidine-1-oxyl and
2,2-dimethyl-6,6-diethyl-4-stearoyloxypiperidine-1-oxyl
are excluded.

2. A process for preparing an oligomer, a cooligomer, a polymer or a copolymer (block or random) by free radical polymerization of at least one ethylenically unsaturated monomer/oligomer, which comprises subjecting the composition according to claim 1 to heat or actinic radiation.

\* \* \* \* \*